United States Patent [19]

Blitchington

[11] 4,268,172
[45] May 19, 1981

[54] METHOD OF AND SYSTEM FOR AUTOMATICALLY ADJUSTING A THRESHOLD LEVEL OF A PULSE GENERATING CIRCUIT TO INSPECT A WEB

[75] Inventor: Frank H. Blitchington, Richmond, Va.

[73] Assignee: Western Electric Company, Inc., New York, N.Y.

[21] Appl. No.: 140,560

[22] Filed: Apr. 15, 1980

[51] Int. Cl.³ .................... G01N 21/86; G01N 21/89
[52] U.S. Cl. .................................... 356/431; 250/563
[58] Field of Search .............................. 356/429–431; 250/559, 563

[56] References Cited

U.S. PATENT DOCUMENTS

| | | | |
|---|---|---|---|
| 3,708,678 | 1/1973 | Kreda | 250/219 D |
| 3,846,623 | 11/1974 | Wefers et al. | 235/61.11 |
| 4,002,830 | 1/1977 | Brown et al. | 358/239 |
| 4,040,748 | 8/1977 | Belleson et al. | 356/199 |
| 4,054,360 | 10/1977 | Oosaka et al. | 350/7 |
| 4,205,769 | 6/1980 | Blitchington | 250/563 |

Primary Examiner—John K. Corbin
Assistant Examiner—Bruce Y. Arnold
Attorney, Agent, or Firm—J. B. Hoofnagle

[57] ABSTRACT

A laminate (32), having holes of different sizes and shapes formed therein, is moved above successive scans of light from a light source (48). A light sensor (58), responsive to light passing through each of the holes, develops a light pulse for each hole during each scan having a level proportional to the amount of light sensed. The level of each light pulse is compared with a preset threshold level and a threshold pulse is developed when the light pulse level exceeds the threshold level. The threshold pulse facilitates the reduction of the preset threshold level so that, when the next subsequent light pulse from the same hole exceeds the reduced threshold level, an additional threshold pulse is produced. The threshold pulses are used within a system (46) to generate an indication of the number of holes formed in the laminate (32).

14 Claims, 21 Drawing Figures

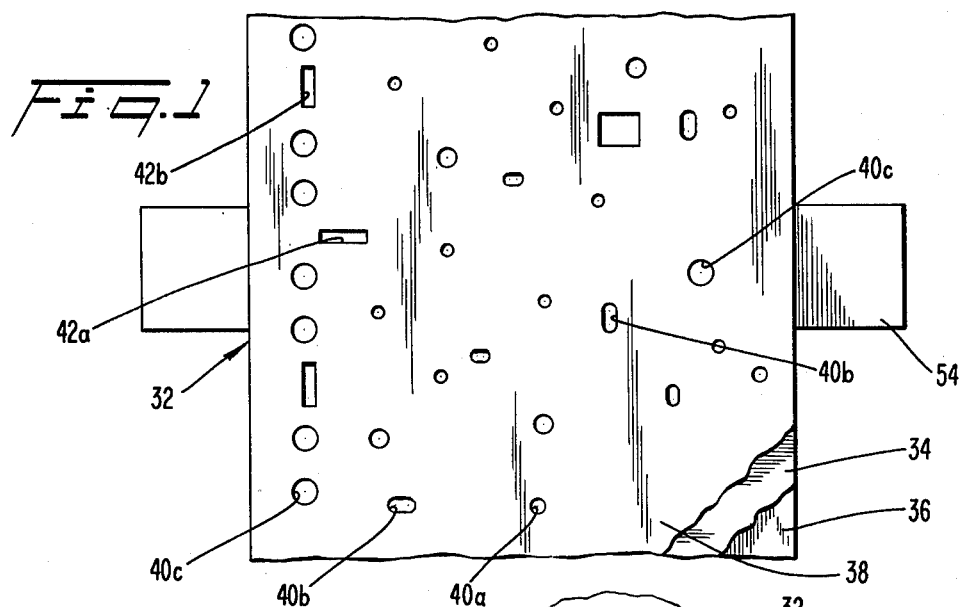
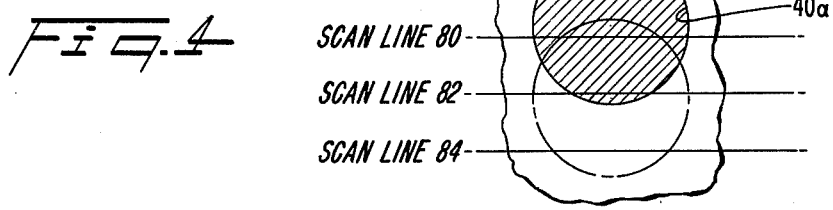
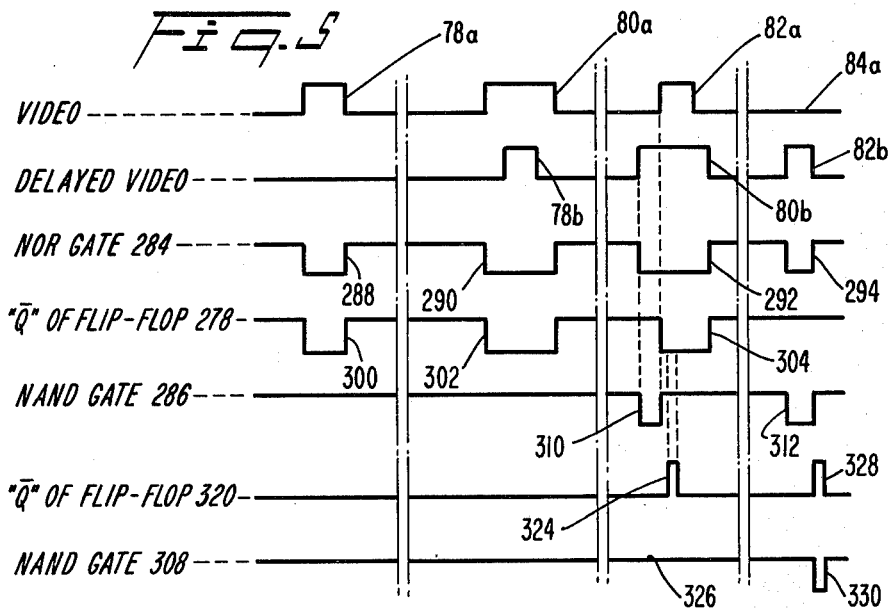

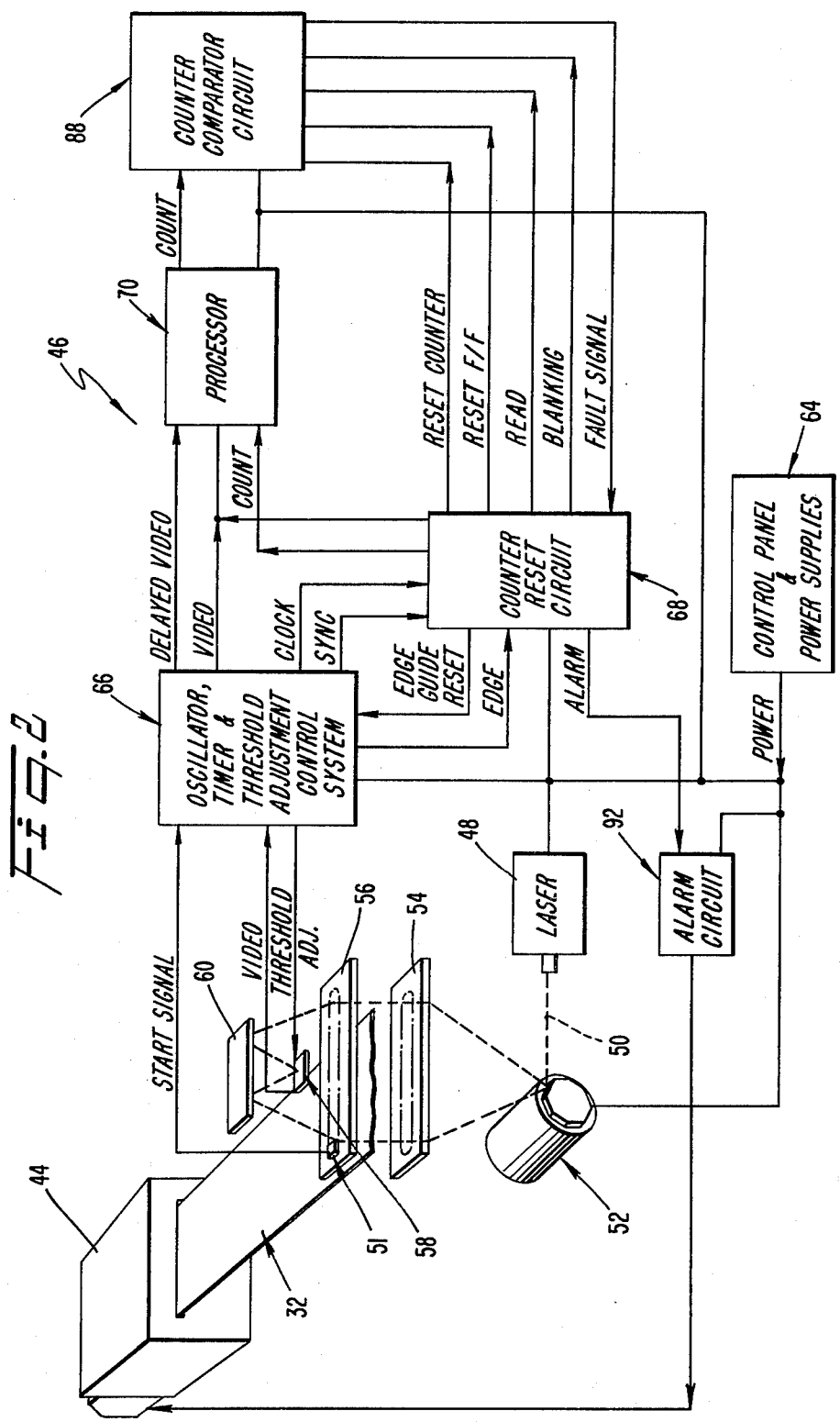

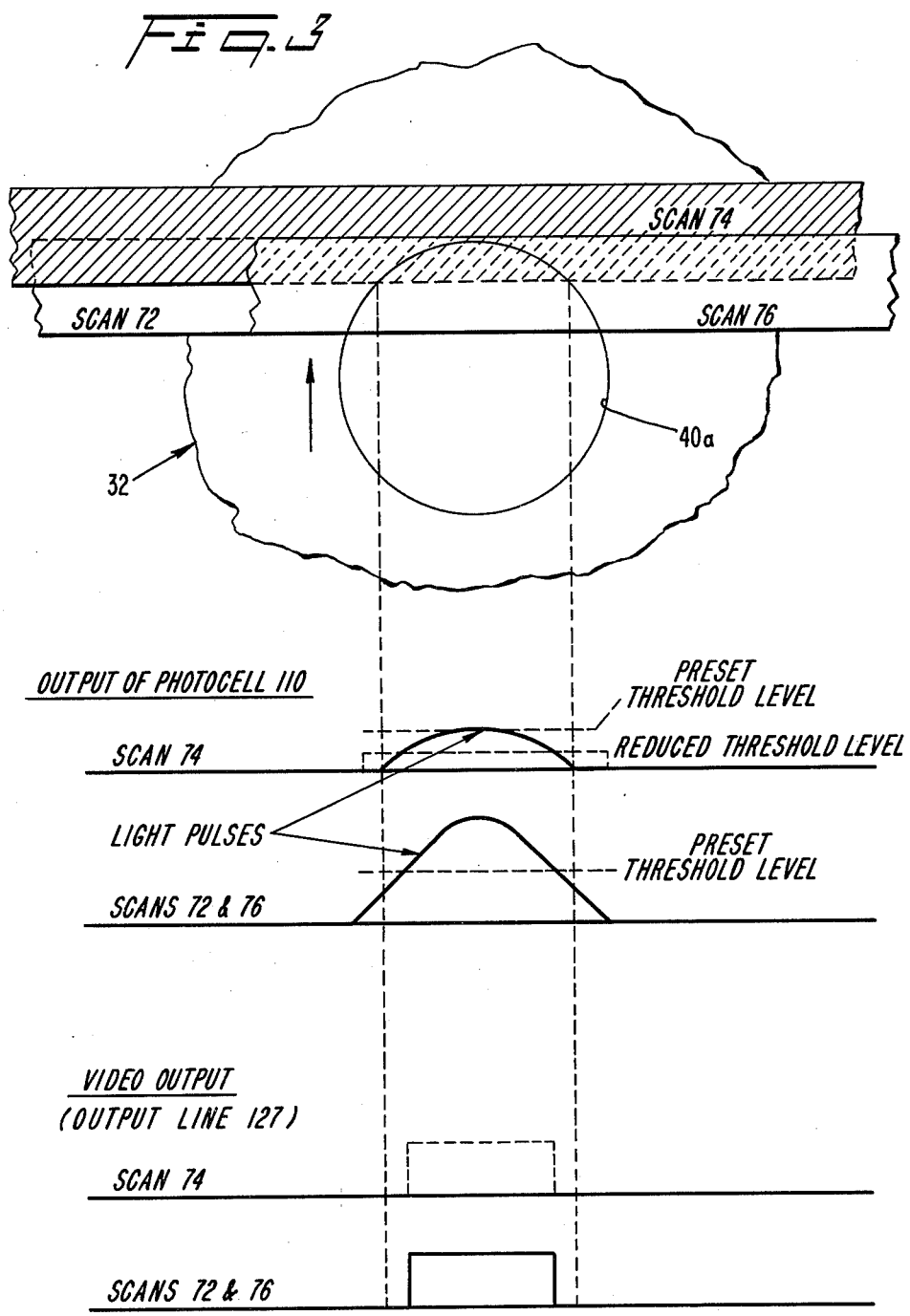

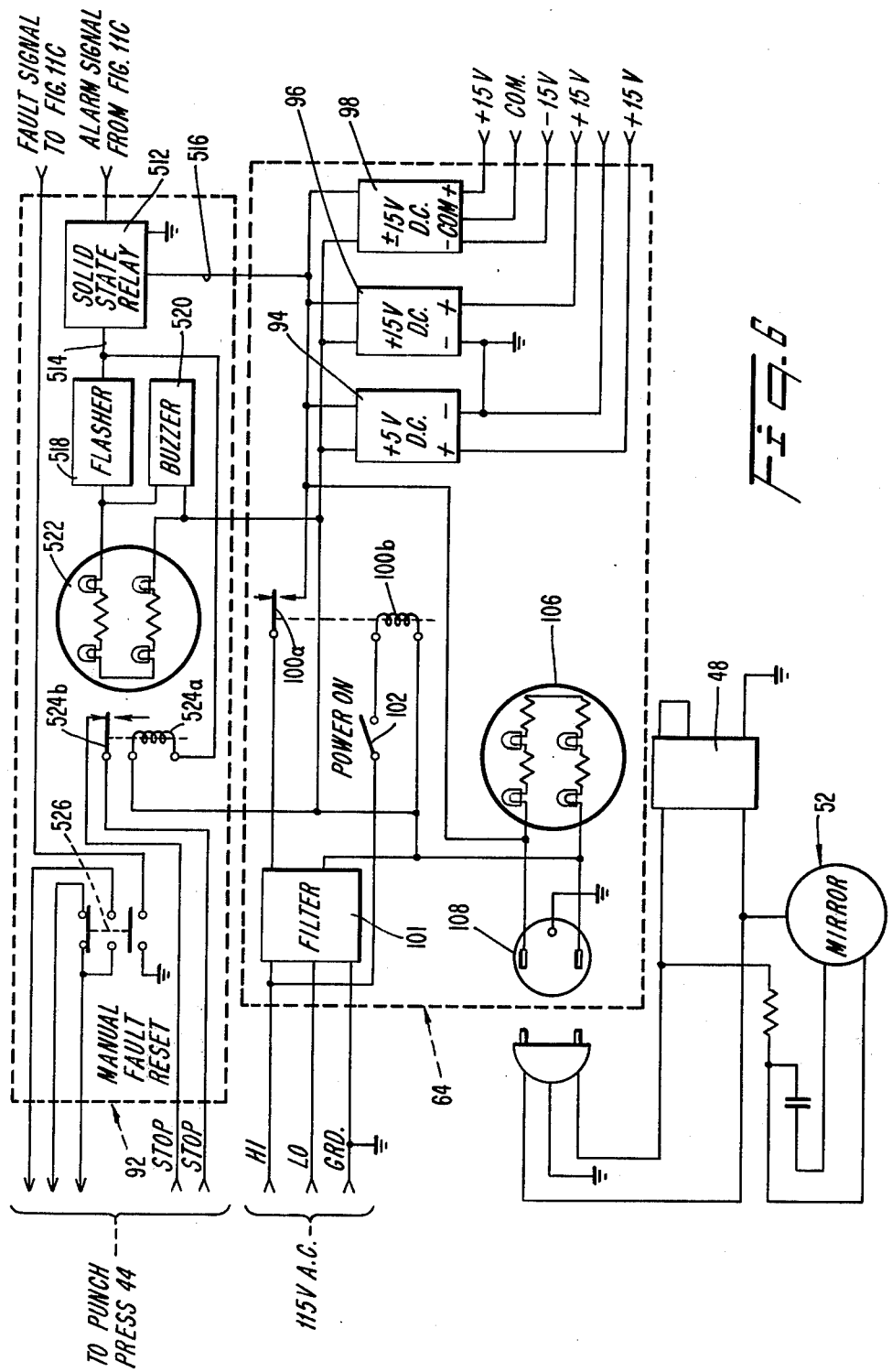

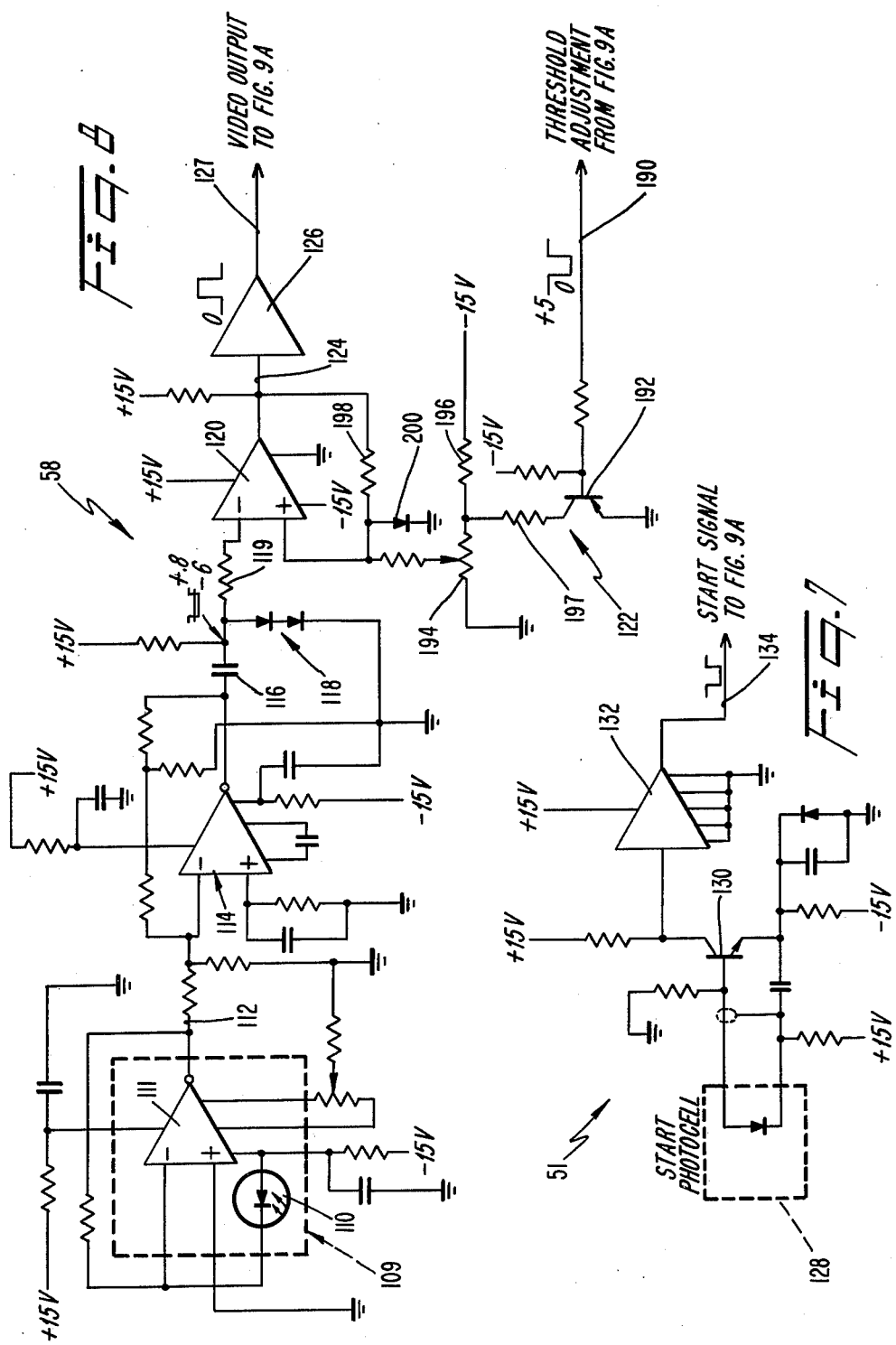

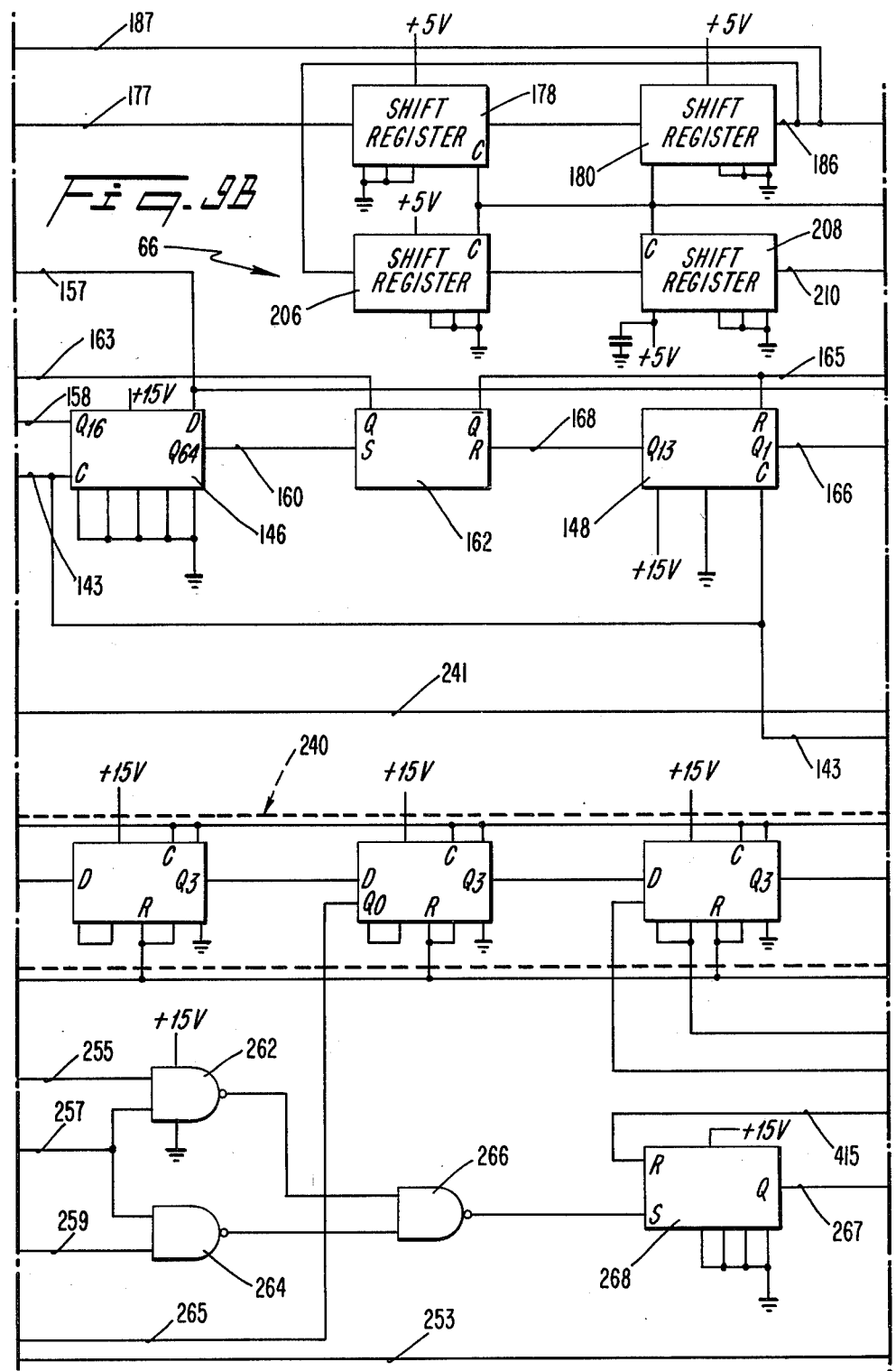

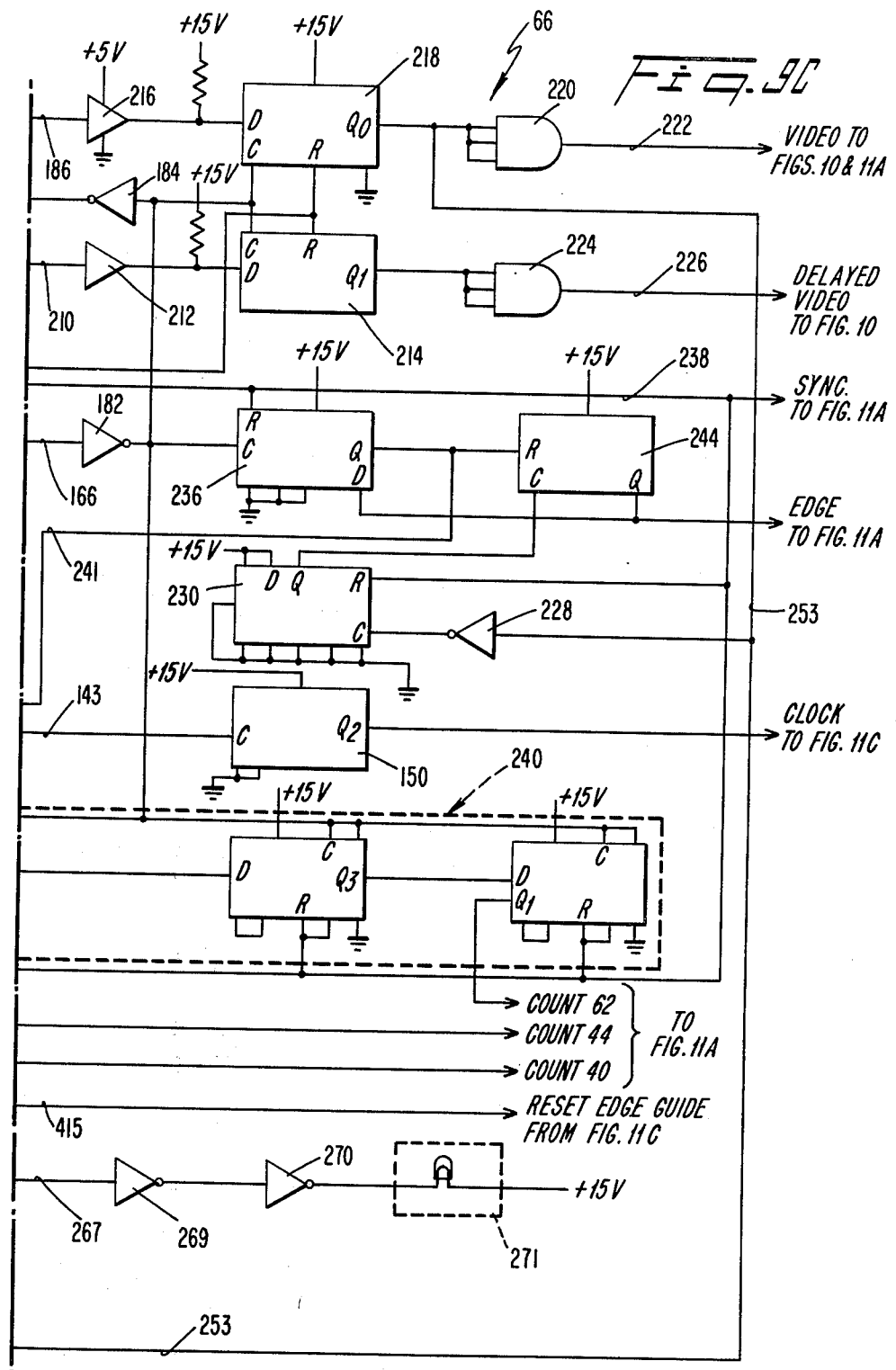

| FIG.11A | FIG.11B | FIG.11C |

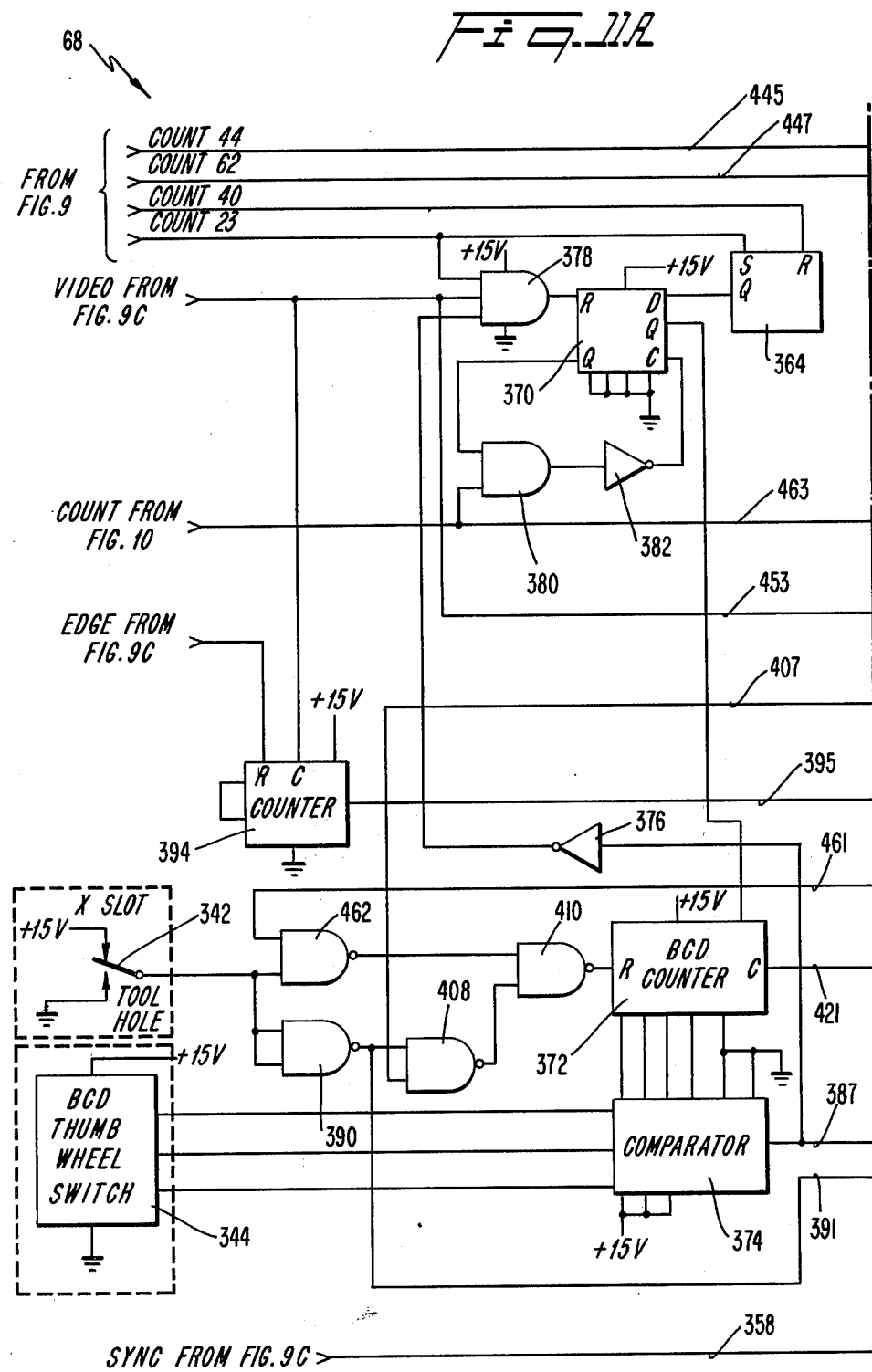

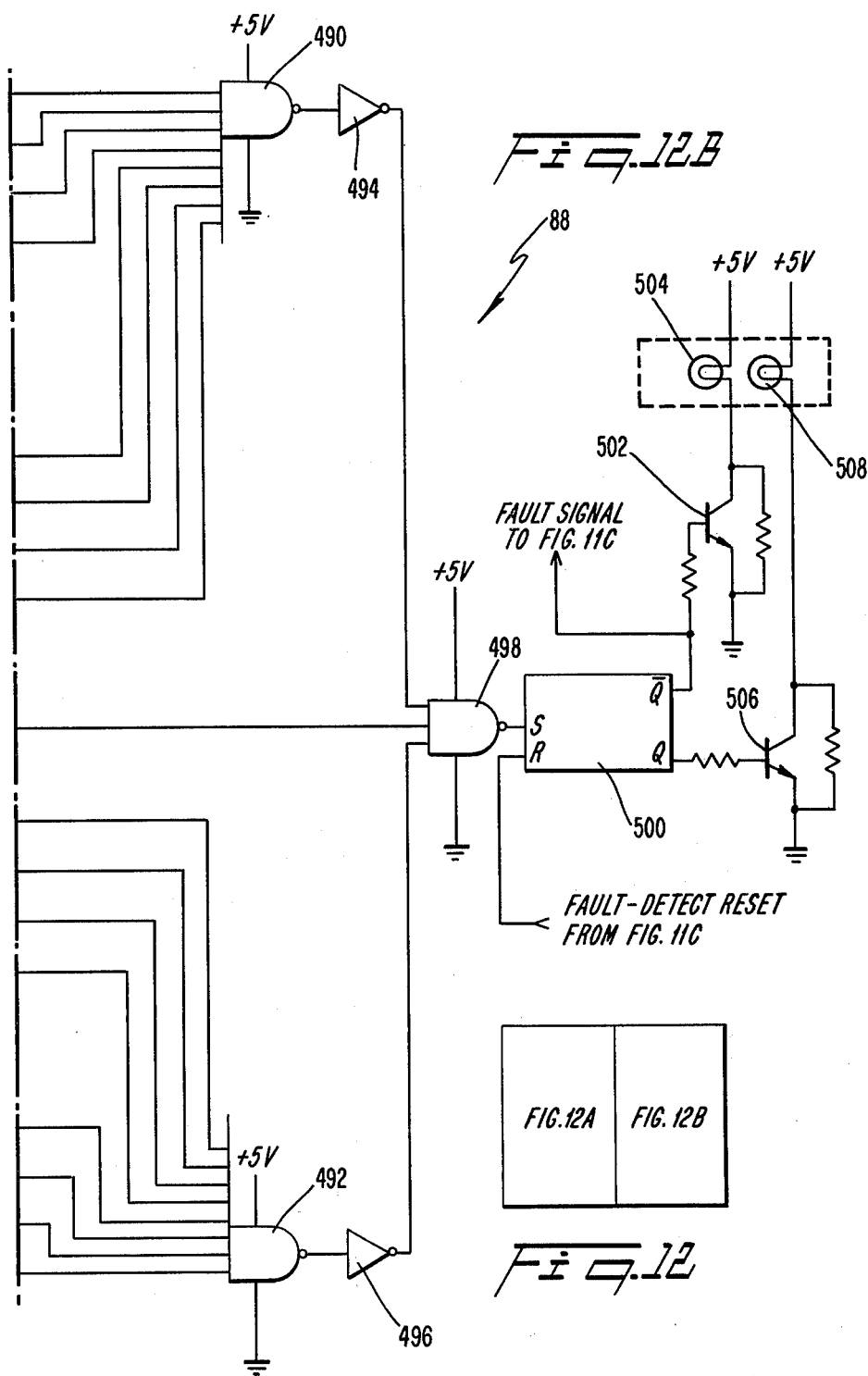

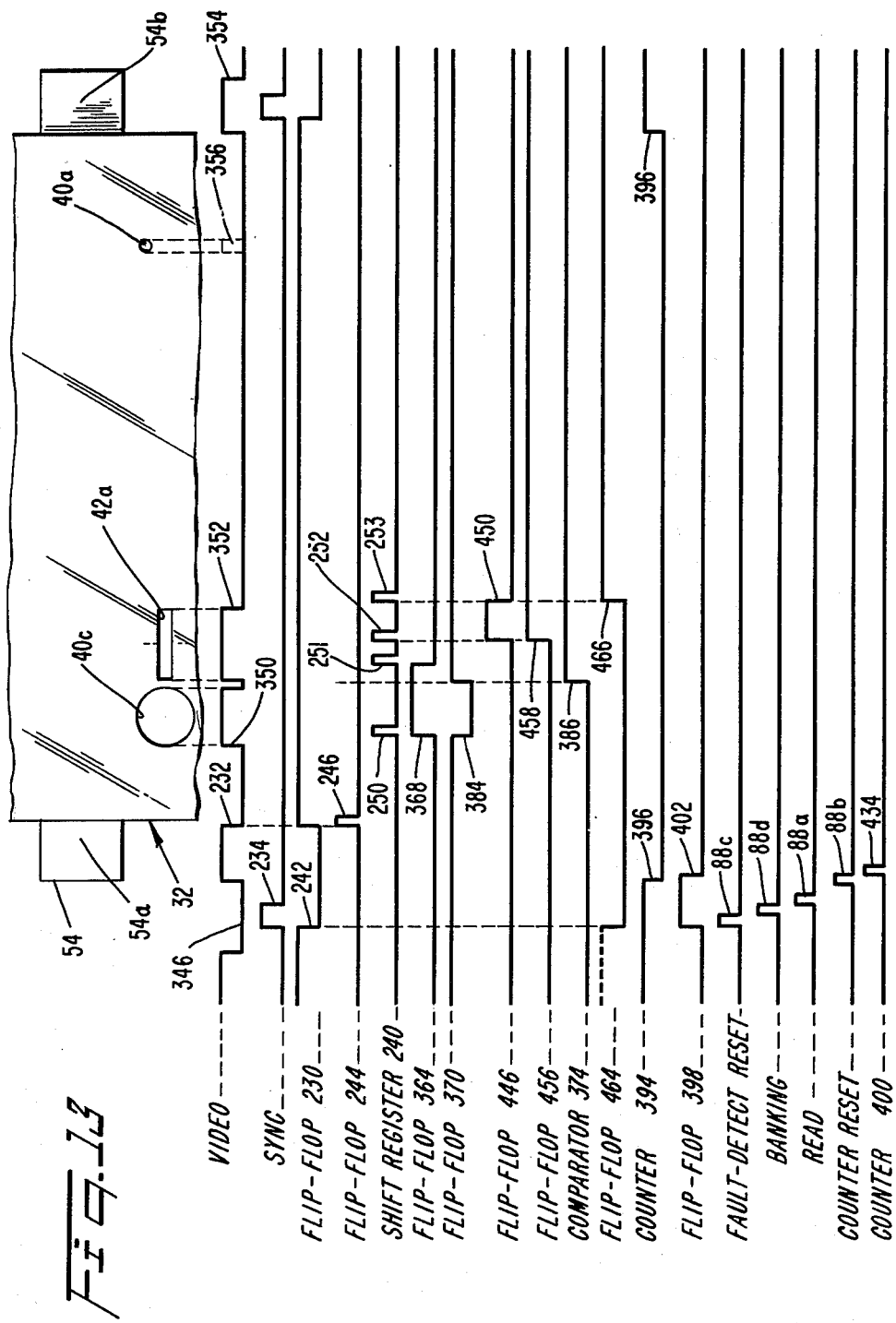

METHOD OF AND SYSTEM FOR AUTOMATICALLY ADJUSTING A THRESHOLD LEVEL OF A PULSE GENERATING CIRCUIT TO INSPECT A WEB

TECHNICAL FIELD

This invention relates to method of and a system for automatically adjusting a threshold level of a pulse generating circuit and, particularly, to methods of and a system for automatically adjusting a threshold level used in an electronic hole counter to prevent undesirable noncoincident scanning of a rotating polyhedral mirror.

BACKGROUND OF THE INVENTION

In the manufacture of flexible and rigid printed circuits, a copper clad laminate is processed through many stations to form the circuits. The laminate initially includes a plastic substrate having copper clad to one or both major surfaces thereof. For flexible printed circuits, the laminate is formed in rolls of substantial lengths, such as 550 feet, and provides a base for the manufacture of many printed circuits of the same pattern formed in successive circuit sections of the laminate. For rigid printed circuits, individual rigid boards of various sizes are each formed as the laminate and provide the base for the manufacture of printed circuits thereon.

Each flexible and rigid laminate is indexed through a punch press to form a plurality of holes and slots therethrough of different sizes and shapes. For example, depending on the code of the circuit to be made, each circuit could have as few as one hole or as many as 9999 holes in each section of the flexible laminate and up to 99,999 holes in each rigid laminate. Many of the holes are extremely small and are usually round while other larger holes may be round, square or oblong. Each hole is required in the ultimate formation of the printed circuit in order for the circuit to perform as designed. Thus, it is critically important that the required number of holes and slots be formed in the copper-clad laminate when indexed through the punch press.

On occasion, the punches of the punch press become worn or damaged, or the punches may be missing. In any case, such defective or missing punches result in a missing hole or holes in successive copper-clad laminates. If the missing holes are not detected, a plurality of copper-clad laminates could be processed through the punch press and through the printed circuit forming facilities. The occurrence of the missing holes would not become apparent until after the actual circuits have been formed and are processed through final testing. Since the holes are through-plated during the manufacturing process, it would be a practical impossibility to drill the holes in the completed circuit where missing holes are detecting during final testing. Consequently, not only would there be a loss of the laminate, there would also be a costly loss in processing time, use of equipment and personnel time.

It is also possible that more than the required number of punches could be included accidently in the punch press which would result in too many holes in each section of the laminate. This may also result in the loss of rolls or boards of laminate.

Thus, it becomes apparent that some form of inspection of the laminate is required as the successive sections exit from the punch press.

Due to (1) the rapid rate at which the laminate moves through the punch press, (2) the minuteness of many of the holes, (3) the number of holes, (4) the different sizes and shapes of the holes and (5) the length of the laminate to be examined, it is a practical impossibility to perform a visual inspection. Thus, it becomes obvious quickly that an automatic hole-detecting system must be used.

Since light can be passed through the holes and slots, it would appear that a light-sensing system operating at a rate compatible with the speed of the moving laminate would be able to count the holes. Further comparison techniques, in the case of the flexible laminate, could be employed to determine whether any of the successive sections contain less than the desired number of holes.

In consideration of a light-sensing system, many side-to-side scans of the moving laminate must be employed to insure that the smallest hole is detected and counted. Due to the minuteness of the small holes, the scan frequency of any light-sensing system used must be sufficient to provide at least one scan line to sense the light passing therethrough. Consequently, the larger holes will be scanned several times. Since the light-sensing system would typically respond and count each time light is sensed, each of the larger holes would provide a light-sensed condition each time it is scanned and thereby provide multiple counts for a single hole. Obviously, a system of this type would not satisfy the requirements of examining a laminate having holes of different shapes and sizes.

In the case of flexible laminate, the pattern of holes and slots is repeated many times along a roll or length of the laminate. If a light-sensing system is used, it must be reset at extremely short intervals to insure that it examines each circuit section with no carryover of hole count from preceding sections.

A system for counting holes in a continuous web or laminate of flexible material is described in a copending application Ser. No. 903,338, (now U.S. Pat. No. 4,205,769) filed on May 5, 1978 in the name of F. H. Blitchington and assigned to the assignee of this application. In that system, the continuous web or laminate of flexible material is indexed through a punch press whereat holes of different shapes and sizes are punched in repetitive patterns through successive sections of the laminate. The laminate is then moved beneath a diffused light source so that light passes through the holes and is sensed by a light-sensing camera which laterally and cyclically scans at a rapid rate the underside of the moving laminate.

During the rapid scanning by the camera, each hole may be scanned many times due to the size and shape of the hole. Consequently, light is sensed many times for the same hole and a corresponding number of signals are developed by the camera. A hole counting system, which receives the developed signal from the camera, includes a delay-and-compare circuit wherein each signal related to a given hole is delayed by one scan cycle and compared with the next signal related to the same hole. When the given hole has passed, the camera does not sense light on the next scanning cycle. This condition, when compared with the immediately previous light-sensed condition, results in the development of an output hole-count pulse from the delay-and-compare circuit.

The count pulses of each section of the laminate are fed to a counter-comparator circuit, and are counted and compared with a desired preset count for each section. If the actual and preset counts of a selected number of successive sections do not compare, an alarm is sounded and a signal is fed to the punch press to stop the punching operation. A detailed description of the system for counting holes in flexible material is provided in the above-mentioned pending application which, by reference thereto, is incorporated herein.

When the above-described system is used for counting holes in a laminate of rigid material, the light from the light source is further diffused as it passes through the hole due to the thickness of the rigid board, thus affecting the operation of the light-sensing camera. A light source such as a collimated laser beam could be used with a rotating polyhedral mirror and two convex lenses to deflect the beam and thereby produce successive parallel beams necessary for side-to-side scans of the moving material. However, if the faces of the rotating polyhedral mirror are not uniformily parallel to the axis of rotation, the laser beam will not trace coincident paths across the material during a complete revolution of the mirror. For example, the scan from a first mirror face which is parallel to the axis could pass light through a given hole, light from a second mirror face which is not parallel to the axis could miss the hole and light from a third mirror face which is parallel to the axis could again pass light through the hole. This would result in a hole count of two when actually there was only one hole.

U.S. Pat. No. 4,002,830, which issued to J. B. Brown et al., discloses an apparatus for compensating for optical error in a rotative mirror. Inherent defects in the angular relationship between facets of a rotating polygonal mirror used to sequentially scan a beam of radiation are corrected by an optical reflecting or refracting element pivotally mounted in the path of the radiation. With the use of electromechanical devices energized by timed electrical signals of appropriate value, the mirror or refracting elements is pivoted to correct the scanning errors caused by angular defects in the rotating mirror. The effects of variations in the angles between facets of the polygonal mirror are also corrected by an electronic circuit which includes a delay capable of delaying the scanning by a predetermined amount. Control means for the electromechanical devices and for the delay device are preprogrammed to make the proper adjustments for each facet of the rotating polygonal mirror.

Consequently, there is a need for a universal system which will count accurately the actual number of holes in both flexible and rigid types of material.

SUMMARY OF THE INVENTION

This invention contemplates a method of and a system for automatically adjusting a voltage threshold level of a pulse generating circuit in response to the generation of pulses at a given fequency. A preset voltage threshold level is compared with the voltage level of each of a plurality of pulses generated at a given frequency. A threshold pulse is developed when the level of one of the generated pulses exceeds the threshold level. The developed threshold pulse facilitates the reduction of the preset threshold level. If the reduced threshold level is exceeded by the level of the next generated pulse, a threshold pulse is developed.

BRIEF DESCRIPTION OF THE DRAWINGS

FIG. 1 is a plan view of a section of the upper side of a flexible laminate having holes of different shapes and sizes formed therethough;

FIG. 2 is a block diagram of a system, which includes a threshold photocell circuit, for examining a moving laminate of the type illustrated in FIG. 1 to count holes in the laminate, detect missing holes and compensate for non-coincident scanning in accordance with certain principles of the invention;

FIG. 3 is a diagram illustrating coincident and non-coincident scans and the technique utilized by the system of FIG. 2 for compensating for the non-coincident scan in accordance with certain principles of the invention;

FIG. 4 is a diagram showing the scanning technique utilized by the system of FIG. 2 for counting the holes in accordance with certain principles of the invention;

FIG. 5 is a waveform timing diagram illustrating the timing relationship between various pulses generated to provide the count of a single hole;

FIG. 6 is a schematic of a power supply, light source, rotating mirror and alarm circuit for the system of FIG. 2;

FIG. 7 is a schematic of a start circuit which is part of, and which provides a pulse to initiate each scan cycle to, the system of FIG. 2;

FIG. 8 is a schematic of a threshold photocell circuit which senses light and provides a video pulse indicating a hole has been located;

FIGS. 9A, 9B and 9C when combined as shown in FIG. 9 show a schematic of an oscillator, timer and threshold adjust system which receives pulses from the start circuit of FIG. 7 and the threshold photocell circuit of FIG. 8 and develops video, delayed video, threshold adjust and various timing pulses to the system of FIG. 2;

FIG. 11 is a view showing a combination arrangement of the schematics of FIGS. 11A, 11B and 11C;

FIGS. 11A, 11B and 11C when combined as shown in FIG. 11 show a schematic of a counter reset circuit which resets a counter-comparator circuit of FIGS. 12A and 12B in accordance with certain principles of the invention;

FIG. 12 is a view showing a combination arrangement of the schematic of FIGS. 12A and 12B;

FIGS. 12A and 12B when combined as shown in FIG. 12 show a schematic of a counter-comparator circuit for visually displaying the hole count and comparing this count with a preset count; and FIG. 13 is a waveform timing diagram showing the relationship between various pulses applied to and developed in the counter reset circuits of FIGS. 11A, 11B and 11C.

DETAILED DESCRIPTION

Figure 9A:
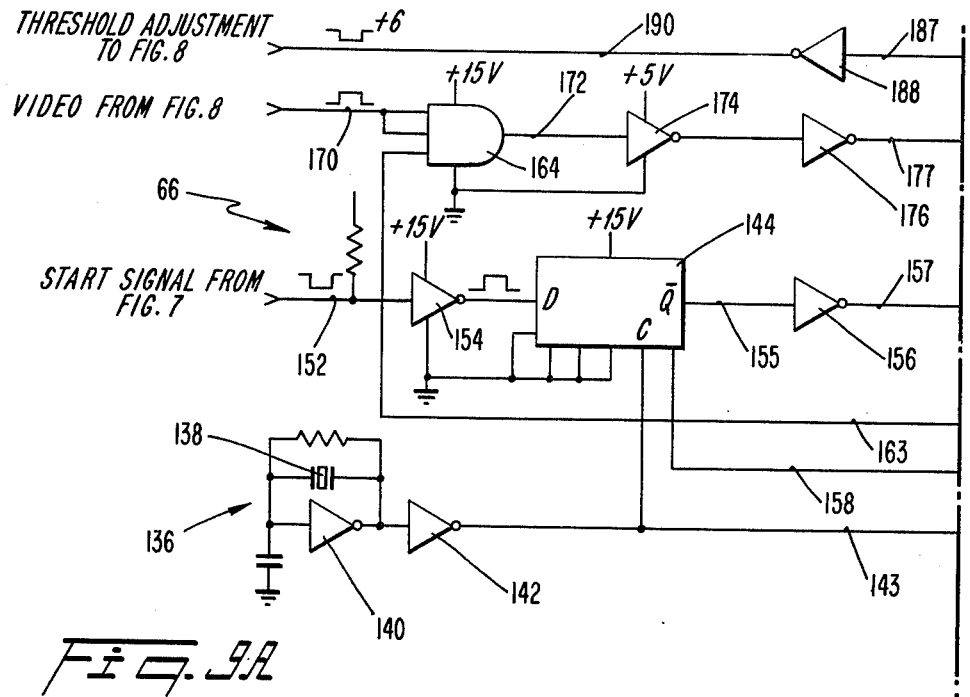
Figure 9:
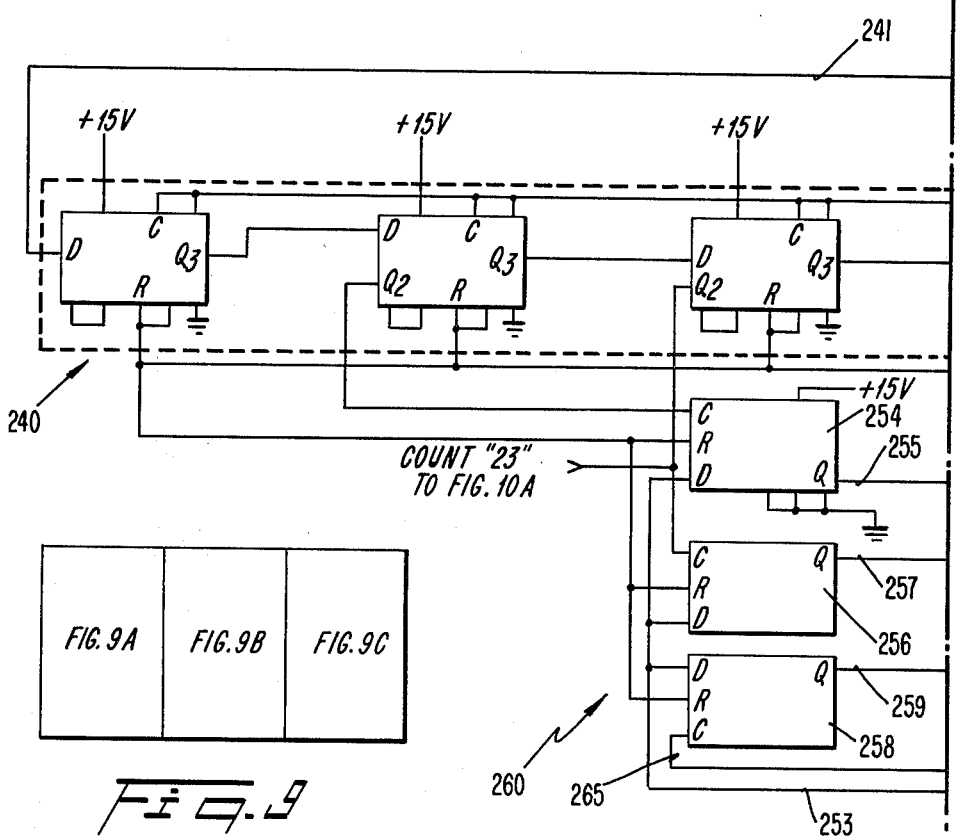
FIG. 9 is a view showing a combination arrangement of the schematic of FIGS. 9A, 9B and 9C.

Referring to FIG. 1, there is illustrated a section of a web such as a flexible laminate, designated generally by the numeral 32. The laminate 32 could include an inner plastic substrate 34 between thin layers 36 and 38 of copper bonded to opposite sides thereof. The flexible laminate 32 can be used in the manufacture of flexible printed circuits (not shown). In order to prepare the laminate 32 for the manufacture of flexible printed circuits, a plurality of holes 40a, 40b and 40c and slots 42a and 42b are punched or formed through the laminate. The holes 40a and 40b ultimately become copper-plated through-holes to electrically link circuit-formed paths of the layer 36 of copper on one side of the inner plastic substrate 34 to circuit-formed paths of the layer 38 of copper on the opposite side thereof. Conventional masking, etching and plating techniques can be employed in the manufacture of printed circuit paths.

The holes 40a and 40b are formed in the laminate 32 and are illustrated as just a few of the many different sizes and shapes of such holes that could appear in the flexible printed circuit. The holes 40c are referred to as tool holes and are used to assist in aligning the laminate 32 as it is located within some of the processing equipment (not shown) used in making the flexible printed circuits. Slots 42a (not shown) are referred to as "X" slots while slots 42b are referred to as "Y" slots. The "X" and "Y" slots 42a and 42b, respectively, are used to precisely align the laminate 32 with masking and printing equipment (not shown).

In the manufacture of the flexible printed circuits, a roll or length of about 550 feet of the laminate 32 is processed through successive stations (not shown) where many printed circuits of a repetitive pattern are formed. The roll of laminate 32 is divided into many successive sections with each section ultimately forming a printed circuit. For example, each successive section could be twelve inches lengthwise of the laminate 32 or any other dimension depending on the requirements of the printed circuit being manufactured. Each twelve-inch printed-circuit section is centered about an associated one of the "Y" slots 42a and, depending on the width of the laminate 32, could have as few as one hole or as many as 9999 holes. Code requirements control the number and size of holes 40a, 40b and 40c to be formed in any given circuit section of the laminate 32.

Conventionally, the holes 40a, 40b and 40c, and the slots 42a and 42b, are punched through the laminate 32 within a punch press 44 (FIG. 2). The punch press 44 contains a plurality of punches (not shown) of different sizes and shapes corresponding in number to the holes and slots required for the repetitive-patterned circuits being manufactured. Successive sections of the laminate 32 are indexed through the punch press 44 for the forming of holes 40a, 40b and 40c and the slots 42a and 42b. Therefore, it is readily apparent that many circuit sections, with each section containing many holes, are included in a single roll of 550 feet of the laminate 32.

Since the hole-punched rolls of the laminate 32 are further processed through costly operations in the manufacture of flexible printed circuits, it is important that the punching operation be stopped as soon as it is determined that the proper number of holes are not being punched in each circuit section of the laminate. The punching of less than the required number of holes could be caused, for example, by broken, missing or worn punches.

Due to (1) the required speed of the punching operation, (2) the large number of holes, (3) the different shapes of holes, (4) the minuteness of many of the holes and (5) the length of the laminate to be examined, it is a practical impossibility for a successful visual inspection to determine whether any holes are missing.

GENERAL SYSTEM DESCRIPTION

Referring to FIG. 2, there is illustrated a system, designated generally by the numeral 46, for counting holes 40a, 40b and 40c and the slots 42a and 42b. The system 46 also detects whether there are any holes or slots missing and provides indication of circuit sections having one or more holes missing.

The system 46 includes a light source 48, such as a laser, which directs a beam 50 of light onto surfaces of a rotating polyhedral mirror, designated generally by the numeral 52. The rotating mirror 52, which directs the light beam 50 through a fresnel lens 54, facilitates scanning of the light beam 50 across a lower surface of the moving laminate 32. Light, which is reflected by the mirror 52, is sensed by a start photocell circuit, designated generally by the numeral 51, to initialize the system 46. The light beam 50 is further directed through a second fresnel lens 56 located above the laminate 32 and is reflected by a mirror 60 onto a light sensor, such as a threshold pulse generating circuit, designated generally by the numeral 58.

The light source 48 is available from Metrologic Instruments, Inc. of Bellmawr, N.J. and is identified as Model ML650. The rotating polyhedral mirror 52 is available from Lincoln Laser Company of Phoenix, Ariz. and is identified as Model PO 06-173-050.

The system 46 further includes a power supply and control circuit, designated generally by the numeral 64, which provides operating power to the various components of the system. An oscillator, timer and threshold adjust control system, designated generally by the numeral 66, provides a 500 kilohertz clock signal which is coupled to a counter reset circuit, designated generally by the numeral 68. The system 66 also provides a threshold adjust control signal which is coupled to the threshold pulse generating circuit 58 to compensate for non-coincident scanning caused by surfaces of the rotating mirror that are not parallel to the rotating axis. The system 66 further provides video and delayed video pulses to a processor circuit, designated generally by the numeral 70, and various count signals to synchronize the system 46.

Referring to FIG. 3, there is illustrated a representation of the hole 40a in the laminate 32. Representations of three successive scans 72, 74 and 76 are illustrated as scans reflected from three successive faces of the rotating mirror 52. It is to be understood that, ideally each mirror face will direct the reflected light over a scan path which is the same path of all previous scans. Therefore, all scans should ideally be coincident in the path that is scanned. In FIG. 3, the laminate 32 is moving in the direction of the arrow 33. Therefore, while the scans ideally are coincident and follow the same path, successive scans pass over advancing portions of the hole 40a. Scan lines 72 and 76 are coincident scans which means that their respective mirror faces are parallel to the axis of rotation and flat whereby the reflected light clearly passes through the hole 40a. Scan 74 is a non-coincident scan which may be caused by its respective mirror face not being parallel to the axis of rotation or the mirror face may not be absolutely flat. Regardless, non-coincident scanning may cause an erroneous count to be developed. Referring to FIG. 3, when scan 72 occurs, the amount of light passing through hole 40a and sensed by the pulse generating circuit 58 results in a light pulse being developed which exceeds a preset threshold level. Thus, the hole 40a represents a light emittable area of the laminate 32. When the developed light pulse exceeds the threshold level, a video or threshold pulse is produced which indicates a light-present condition. When scan 74 occurs, the amount of light passing through hole 40a and sensed by the circuit 58 results in a light pulse which does not exceed the preset threshold level and does not produce a video pulse. This represents a no-light condition. When scan 76 occurs, the amount of light passing through hole 40a and sensed by the circuit 58 again results in the development of a light pulse which exceeds the preset threshold level and produces a video pulse. Since scan 74 occurs between scans 72 and 76, the no-light condition resulting from scan 74 occurs between two light-present conditions. Thus a count of two is developed for the same hole 40a.

To compensate for the non-coincident scan 74, a threshold adjust signal is generated within the system 66 in response to the preceding video pulse. Thus results in the reducing of the threshold level, as represented in FIG. 3, to permit the generation of a video pulse in response to the low level light pulse resulting from the non-coincident scan 74.

As the laminate 32 moves past the light source 48, the light beam 50 rapidly scans the width of the moving laminate. Since many of the holes 40a are minute, the scan must be rapid to insure that such minute holes are scanned at least once. Thus, the counting of each hole and slot in the laminate 32 can not be accomplished by the mere sensing of light.

Referring to FIG. 4, there is illustrated a cross-hatched representation of one of the holes 40a in the laminate 32 which is moving in an upwardly direction as shown. Four successive scan lines 78, 80, 82 and 84 represent four scans from successive faces of the rotating mirror 52. Scan lines 78, 80 and 82 clearly pass over the hole 40a whereby the threshold photocell circuit senses the light-present condition and develops a video pulse (FIG. 5) for each of the three scans. In this example, three light-present video pulses 78a, 80a and 82a have been developed in response to a single hole. The next successive scan line, which is scan line 84, then passes adjacent to but not over the hole 40a whereby the threshold photocell circuit 58 does not sense any light at this location. This represents the no-light condition.

In response to light sensed by the threshold photocell circuit 58, the video pulse is developed and is coupled to the processor 70. A delayed video pulse is also developed which is identical to the video signal but which is delayed by a time which is equal to one scan cycle. The time of one scan cycle is equivalent to the time required for the light beam 50 to pass from an entry edge of one face of the mirror 52 to the entry edge of the next face. A representation of the video pulse 86 is illustrated in FIG. 5.

Referring to FIGS. 4 and 5, pulses 78a, 80a and 82a represent the video pulses developed in response to light sensed at hole 40a during scan lines 78, 80 and 82, respectively. The amount of light sensed during scan lines 78 and 82 is less than that sensed during scan line 80 due to the fact that scan line 80 passes through the center or larger portion of the hole 40a. Consequently, the pulse width of pulses 78a and 82a are less than the width of pulses 80a. Also, there is no light sensed during scan line 84. Therefore, no pulse appears at 84a of the video line of FIG. 5.

The video pulses 78a, 80a and 82a are fed to the control system 66 and are initially delayed for a period equal to the time for one scan cycle as previously noted. Thus, as illusted in FIG. 5, pulse 78b represents delayed pulse 78a and occurs coincidentially with the next developed video pulse 80a. The delay effected within the control system 66 has the effect of shifting the hole 40a to a position as shown in phantom in FIG. 4.

The video pulses 78a. 80a and 82a as well as the delayed pulses 78b, 80b and 82a as well as the delayed pulses 78b, 80b and 82b are coupled to the processor 70. The processor 70 generates an output count pulse only after the scan line 84 has passed the area adjacent to the hole 40a and no light was sensed by the threshold pulse generating circuit 58.

The count pulse is then coupled to a counter-comparator circuit, designated generally by the numeral 88. The counter-comparator circuit 88 includes facilities for establishing a preset count by manual adjustment. The preset count represents the desired number of holes 40a, 40b and 40c and slots 42a and 42b within each circuit section of the laminate 32. As the count pulses enter the counter-comparator circuit 88, they are processed through a counter portion of the circuit to provide an actual hole count which is compared with the preset count within a comparator portion of the circuit. Also, visual-count displays provide a final hole count for each circuit section of the laminate 32. If the actual count and the preset count compare favorably, a visual indication is provided and the hole punching operation continues.

If the actual count does not compare favorably with the preset count, a fault signal is developed by a fault signalling portion of the circuit 88 and represents that a circuit section having one or more missing or extra holes has been detected. The fault signal is then coupled to the counter reset circuit 68 which includes facilities for manually presetting a count representing the number of successive circuit sections with missing holes which will render the entire roll unacceptable. The count of the fault signal is compared with the preset count and if the preset count is reached, the counter reset develops an alarm signal which is coupled to an alarm circuit, designated generally by the numeral 92. Upon reception of the alarm signal, the alarm circuit 92 controls the sounding of an alarm and sends a "stop" signal to the punch press 44 to stop the punching operation.

The counter reset circuit 68 also receives a video signal, a sync signal, an edge signal and a clock signal from the system 66 and a count pulse from the processor 70. This combination of signals being fed to the counter reset circuit 68 controls facilities within the circuit to provide, as represented in FIG. 12, a "read" pulse 88a a "counter" pulse 88b, a "fault-detect reset" pulse 88c and a "blanking" pulse 88d which are coupled to the counter-comparator 88.

When the scanning of a given circuit section of the laminate 32 has been completed, the "read" pulse 88a is developed by the counter reset circuit 68 and signals the counter-comparator circuit 88 to produce the comparison results between the actual hole count and the preset count as discussed above. The "read" pulse 88a also controls the visual-count displays to provide a read-out of the actual hole count.

When the comparison results have been "read," and "counter reset" pulse 88b is coupled to the counter-comparator circuit 88 to reset the counter portion in preparation for the counting of the holes of the next circuit section of the laminate 32. Also, the "fault detect reset" pulse 88c is coupled to the counter-comparator circuit 88 to reset the fault signal portion in the event that this portion had been activated.

During the period when the system 46 is being reset, the "blanking" pulse 88d is fed to the counter-comparator circuit 88 to momentarily turn off the visual-count displays to provide visual indication that the system is functioning properly.

Start Photocell Circuit 51

Referring to FIG. 7, the start photocell circuit 51 includes a photocell 128. The photocell 128 is manufactured by United Detector Technology of Santa Monica, California as their type UDT Pin Spot 2D. When light is sensed by the photocell 128, a positive voltage is applied to the base of transistor 130 and turns on the transistor. A negative going pulse, which now appears at the collector of transistor 130, is coupled through buffer 132. The buffer 132 is of the type identified as a MC14050 noninverting hex buffer and described in a publication by Motorola Incorporated entitled "McMos Integrated Circuits Data Book" hereinafter referred to as the "Data Book." The negative going pulse, which appears on output line 134, is used as a "start" signal to facilitate the control of circuits contained within the system 66 to receive the video pulse generated by the threshold pulse generating circuit 58.

Threshold Pulse Generating Circuit 58

Referring to FIG. 8, the threshold pulse generating circuit 58 includes a photocell-detector unit designated generally by the numeral 109. The unit 109 includes a photocell 110 and an amplifier 111. The photocell-detector unit 109 is manufactured by United Detector Technology of Santa Monica, California, as their type UDT 600. When the photocell 110 senses light from the light source 48, the positive going light pulse is developed on output line 112. Output line 112 is coupled to a negative input of an inverting amplifier designated generally by the numeral 114. The inverting amplifier 114 is manufactured by Reticon Corporation of Sunnyvale, California, as their type CA10A. The amplifier 114 is biased in a conventional manner. A positive input of the amplifier 114 is coupled through a parallel R-C network 115 to ground. The output of the amplifier 114 is coupled to a capacitor 116 to remove any d.c. signal from the output signal produced by the amplifier. During periods when no light is sensed by the photocell 110, a pair of diodes, designated generally by the numeral 118, which are coupled to the capacitor 116 normally clamp the output level of the amplifier 114 to a maximum of eight-tenths of a volt.

Since the amplifier 114 is an inverting amplifier, the positive going light pulse produced by the photocell 110 is converted to a negative going pulse. The negative going pulse reverse biases the diodes 118 to facilitate coupling of the negative going pulse through resistor 119 to a negative input of a comparator 120. The comparator 120 is manufactured by Precision Monolithics, Inc. of Santa Clara, California, as their type CMP-01. A positive input of the comparator 120 is coupled to a threshold adjust circuit designated generally by the numeral 122. If the voltage level of the pulse which appears on the negative input of the comparator 120 exceeds a voltage threshold level signal which appears on the positive input of the comparator, a positive going video or threshold pulse is produced on output line 124.

The output line 124 is coupled to a buffer 126 to provide for a video pulse of fifteen volts to pass through a coaxial cable (not shown) to the system 66 (FIGS. 2, 9A, 9B and 9C). The buffer 126 is of the type identified in the Data Book as an MC14050 hex non-inverting buffer. The video pulse appearing at the output of buffer 126 on output line 127 represents the video pulse as illustrated on the "video" line of FIG. 5.

Power Supply and Control Circuit 64

Referring now to FIG. 6, the power supply and control circuit 64 includes a D.C. power supply 94 which provides five volts output. The power supply 94 is available from the Acopian Corporation of Easton, Pennsylvania as Model Number 5EB250. The circuit 64 also includes a D.C. power supply 96 which provides fifteen volts output. The power supply 96 is available from the Acopian Corporation as Model Number 15EB20. Further, the circuit 64 includes a D.C. power supply 98 which provides a positive and a negative fifteen volts output. The power supply 98 is available from the Acopian Corporation as Model Number 5E25DD15805. Each of the power supplies 94, 96 and 98 is connectable to an external source of 115 volts A.C. through a relay contact 100a and a filter 101. When a power switch 102 is closed, a relay coil 100b is energized to close contact 100a and connect the filtered 115 volts A.C. to the power supplies 94, 96 and 98. Also, a lamp 106 is operated to indicate that external power is being applied to the power supply and control circuit 64.

When the switch 102 is closed, the filtered 115 volts A.C. is coupled to an outlet 108. Outlet 108 provides power access for the light source 48 and the rotating mirror 52.

Oscillator, Timer and Threshold Adjust Control System 66

Referring to FIGS. 9A, 9B and 9C, an oscillator, designated generally by the numeral 136, includes a 4 MHz crystal 138 which is connected across an inverting buffer 140 to provide a 4 MHz signal from the output of the combination thereof. The inverting buffer 140 is of the type identified in the Data Book as MC14049 hex inverter-buffer. The 4 MHz signal is coupled through another inverting buffer 142, of the same type as buffer 140, and is fed over line 143 to (1) a clock "C" input of a flip-flop 144, (2) a clock "C" input of a 64-bit shift register 146, (3) a clock "C" input of a 14-bit binary counter 148 and (4) a clock "C" input of a 12-bit binary counter 150. The Data Book identifies the flip-flop 144 as MC14013, the 64-bit shift register 146 as MC14517, the 14-bit binary counter 148 as MC14020 and the 12-bit binary counter 150 as MC14040.

The start signal is fed from output line 134 (FIG. 7) to input line 152 of the system 66. The start signal is fed through an inverting buffer 154, of the same type as buffer 140, to a data (D) input of the flip-flop 144 to set the flip-flop on the next output pulse of the oscillator 136. When the flip-flop 144 is set, the "$\overline{Q}$" output is a negative-going signal on line 155. The negative-going signal on line 155 is fed through an inverting buffer 156, of the same type as buffer 140 over line 157 to a data (D) input of the shift register 146. The negative-going signal is shifted through the shift register 146 at a clock rate of 4 MHz. After the negative-going signal has been shifted to the sixteenth position of the shift register 146, an output signal is generated on line 158 to reset the flip-flop 144. When the negative-going signal has been shifted to the sixty-fourth position of the shift register 146, an output signal is generated on line 160 which is coupled to the set (S) input of a flip-flop 162 to set the flip-flop. When the flip-flop 162 is set, the "Q" output is a positive-going pulse and is fed over line 163 to one input of AND gate 164. The flip-flop 162 and the AND gate 164 are of the type identified in the Data Book as an MC14013 dual type D flip-flop and MC14073 triple 3-input AND gate, respectively. The "Q̄" output of the flip-flop 162 is fed over line 165 to the reset (R) input of the counter 148. The counter 148 is driven by the oscillator 136, and generates a 2 MHz clock signal on line 166. The time required for a scan cycle is the time required for the light reflected by one mirror surface of the rotating mirror 52 to travel across the laminate 32 and is equivalent to the time period for 2048 pulses at the 2 MHz frequency. The counter 148 also generates an output pulse on line 168 after 2048 pulses of the oscillator 136. The output pulse on line 168 is coupled to the reset (R) input of the flip-flop 162. Thus the positive-going pulse on the "Q" output of flip-flop 162 has a pulse width of 2048 pulses.

The video pulse (FIG. 5) is fed from output line 127 (FIG. 8) to input line 170 of the system 66. The video pulse is fed to two inputs of the AND gate 164 whereby a pulse, similar to the video pulse, appears on output line 172 if the positive-going signal is present on the "Q" output of flip-flop 162. The signal on output line 172 is coupled through two inverting buffers 174 and 176 to provide sufficient power for the video pulse which is then fed over line 177 to two series-connected TTL-compatible 1024-bit shift registers 178 and 180. The inverting buffers 174 and 176 are identified in the Data Book as MC14049. The shift registers 178 and 180 are identified as 1024-bit shift registers manufactured by Synertek, Inc. of Santa Clara, California as their type 2833A. The 2 MHz signal, which is present on line 166 of counter 148 is coupled through inverting buffers 182 and 184 to the clock (C) inputs of the shift registers 178 and 180. Since shift registers 178 and 180 are connected in series, the video pulse, which enters shift register 178, is shifted by 2048 pulses of the clock signal before the video pulse appears on output line 186. Thus, the video pulse developed by the threshold photocell circuit 58 will exit the shift registers 178 and 180 before the next successive video pulse enters the shift registers. The pulse appearing on output line 186 is fed over line 187 to an inverting buffer 188 and provides the threshold adjust signal on output line 190.

Referring to FIG. 8, if no light has been sensed previously by the threshold photocell 110, transistor 192 is off and the voltage threshold level is established by the potential across a potentiometer 194 due to a negative voltage source coupled through resistor 196. The potential that is present on the positive input of the comparator 120 is the preset threshold level referred to hereinabove. When light is sensed by the photocell 110, the light pulse from the photocell is amplified by the inverting amplifier 114. The light pulse is coupled through capacitor 116 to the negative input of the comparator 120. If the light pulse on the negative input of the comparator 120 does not exceed the preset threshold level, output line 124 remains at a low level and the preset threshold level is not changed.

When the level of the light pulse on the negative input of the comparator 120 exceeds the preset threshold level on the positive input, the positive-going video or threshold pulse is developed and appears on the output line 124. The video pulse is coupled to the system 66 (FIGS. 9A, 9B and 9C) through the buffer 126. If flip-flop 162 (FIG. 9B) has been set, the video pulse is coupled to the shift registers 178 and 180. The output of the buffer 188 is the threshold adjust signal which is fed over line 190 to transistor 192 as a negative going signal. The threshold adjust signal turns on transistor 192 and couples a resistor 197 to ground potential whereby the potential across the potentiometer 194 is reduced from a negative potential to a potential approaching zero volts. This circuit configuration reduces the amount of voltage across the potentiometer 194 thus reducing the negative threshold level present on the positive input of the comparator 120. A resistor 198 and a diode 200 are included in a feedback path of the comparator 120 to provide for hysterisis when the comparator changes states.

Prior to the sensing of light through one of the holes 40a, 40b or 40c by the pulse generating circuit 58, the threshold level is preset at a relatively high level. This prevents development of a video pulse in response to random light reaching the pulse generating circuit 58 other than through one of the holes. As noted above, when a non-coincident scan, such as scan 74, scans tangentially of the holes 40a, for example, the amount of light sensed by the circuit 58 is minimal. Even though the resulting light pulse is amplified significantly by the amplifier 144, the pulse is still of insufficient amplifitude to exceed the preset threshold level. However, once the preset threshold level has been exceeded by an incoming light pulse, the threshold adjust circuit 122 is controlled to reduce the threshold level. This insures that subsequent light pulses developed in response to any particular hole, including non-coincident tangential scans such as scan 74, will lead to the development of video pulses to maintain continuity in video pulse generation for that given hole. This avoids a two-count indication when a single hole is being scanned.

Referring further to FIGS. 9A, 9B and 9C, the output line 186 (FIG. 9B) is coupled to a second 2048-bit shift register which includes two series-connected 1024-bit shift registers 206 and 208. The shift registers 206 and 208 are of the same type as shift register 178. The shift registers 206 and 208 are clocked by the same clock signal as shift registers 178 and 180. An output which appears on output line 210 of shift register 208 is the same signal which appeared earlier on output line 186 by a time equal to one scan cycle. Thus shift registers 206 and 208 generate a delayed video pulse. The delayed video pulse is fed over line 210 (FIGS. 9B and 9C) to a buffer 212 which feeds a data (D) input of shift register 214. The buffer 212 is manufactured by Motorola, Incorporated and is identified as MC7407 hex buffer-driver with open-collector high voltage outputs. The shift register 214 is of the type identified in the Data Book as MC14015 dual four-bit static shift register. The video pulse appearing on output line 186 is also fed through a buffer 216 (FIG. 9C) to a data (D) input of shift register 218. The buffer 216 and the shift register 218 are of the same type as buffer 212 and shift register 214, respectively. The shift registers 214 and 218 are clocked by the same 2 MHz signal which clocks shift registers 178, 180, 206 and 208 and is reset by the "Q̄" output of flip-flop 162. The resetting of shift registers 214 and 218 occur at the beginning of each scan cycle. The "Q" output of the flip-flop 218 is coupled to an AND gate 220 thus providing the video pulse on output line 222. The "Q" output of flip-flop 214 is coupled to an AND gate 224 thus providing the delayed video pulse on output line 226.

The video pulse (FIG. 13) from the "Q" output of flip-flop 218 also is fed to an inverting buffer 228 thus producing an inverted video pulse. It is noted that the inverted video pulse is merely an inverted version of the video pulse illustrated in FIG. 13 and, therefore, is not illustrated. Thereafter, the inverted video pulse is fed to the clock (C) input of flip-flop 230 which will set the flip-flop during the positive transition of the inverted signal. Referring to FIG. 13, when the trailing edge of video pulse 232 occurs, the first positive transition of the inverted video pulse also occurs. This condition occurs when light, which is directed through the lens 54, is blocked by the edge of the laminate 32. Thus the edge of the laminate 32 is thereby detected and can be used as a reference point for subsequent circuit operations during this scan cycle. Even though the laminate 32 may shift or skew during subsequent scan cycles, the operational cycle of the counter reset circuit 68 is started only when the edge of the laminate 32 is detected as represented by the positive going, trailing transition of the inverted video pulse and the setting of the flip-flop 230. Thus each scan cycle will have the same starting point reference, i.e., the edge of the laminate 32.

At the beginning of a new scan cycle, the start signal is generated and produces a "sync" pulse 234 (FIG. 13), which appears on the data (D) input of shift register 146 (FIG. 9B). The sync pulse 234 is fed to (1) the reset "R" input of flip-flops 230 and 236 (FIG. 9C) and (2) to output line 238 and (3) to shift register, designated generally by the numeral 240 over line 239. Flip-flops 230 and 236 are identified in the Data Book as MC14013 dual D-type flip-flop. The shift register 240 produces various count pulses. When flip-flop 230 is reset, the "Q" output goes negative, as illustrated by the negative pulse 242 (FIG. 13), during the leading positive transition of the sync pulse 234 (FIG. 13). By application of the sync pulse 234, the counter reset circuit 68 is prepared to receive incoming data for the ultimate resetting of the counter comparator circuit 88.

When the flip-flop 230 is being set, the pulse 242 goes positive and is fed to the clock (C) input of a flip-flop 244. This results in the development of a positive pulse 246 (FIG. 13) at the "Q" output of flip-flop 244 which is fed to the data (D) input of flip-flop 236. It is noted that the leading edge of pulse 246 is coincident with the edge of the laminate 32, as illustrated in FIG. 13, and is referred to as the "edge" pulse. Pulse 246 is also fed to output line 247. Flip-flop 236 is clocked by the 2 MHz frequency signal and is set by the next pulse therefrom. The setting of flip-flop 236 produces a positive going pulse on its "Q" output. This positive going pulse is fed to the reset (R) input of flip-flop 244 and to terminate the "edge" pulse 246 (FIG. 13). The "Q" output of flip-flop 236 is also fed to a data (D) input of shift register 240 (FIG. 9A) over line 241. The shift register 240 includes eight series-connected shift registers identified in the Data Book as MC14015 four-bit shift registers. Shift register 240 then processes the pulse from flip-flop 236 therethrough at the 2 MHz clock frequency and provides several outputs at different count levels of eleven, twenty-three, thirty-seven, forty, forty-four and sixty-two. Count twenty-three, forty, forty-four and sixty-two pulses are represented on the pulse line (FIG. 13) of shift register 240 as pulses 250, 251, 252 and 253, respectively.

The video pulse is also fed over line 253 to a data (D) input of flip-flops 254, 256 and 258 (FIG. 9A). Flip-flops 254, 256 and 258 are a part of an edge guide fault circuit designated generally by the numeral 260. The circuit 260 determines if the material has skewed or shifted which may produce an erroneous count by the system 46. This determination is based on the location of a tool hole 40c (FIG. 1) from the edge of the material. If the material has not shifted or skewed, the tool hole 40c will be twenty-three counts from the edge of the laminate 32. The system also determines if the laminate 32 shifted beyond a distance which would not create an erroneous count by the system 46. The circuit 260 is also reset by the sync pulse 234 (FIG. 13).

Count-eleven pulse is fed to the clock (C) input of flip-flop 254. If the video pulse is present on the data (D) input of flip-flop 254 when count-eleven pulse is fed to the clock input, the flip-flop is set. The "Q" output of flip-flop 254 is fed over line 255 to one input of NAND gate 262. Count-twenty-three pulse 250 is fed to the clock (C) input of flip-flop 256 and sets the flip-flop, if the video signal is present on the data (D) input. The "Q" output of flip-flop 256 is fed over line 257 to an input of the NAND gate 262 and to an input of NAND gate 264. Count-thirty-seven pulse is fed over line 265 (FIG. 9B) to the clock (C) input of flip-flop 258 which sets the flip-flop, if the video pulse is present on the data (D) input. The "Q" output of flip-flop 258 is fed over line 259 to an input of the NAND gate 264. The outputs of NAND gates 262 and 264 are coupled to inputs of NAND gate 266. The output of NAND gate 266 is coupled to a set (S) input of flip-flop 267. When either of the flip-flops 254 or 258 is set, an erroneous condition exists which indicates that the laminate has shifted and the tool hole 40c was not found after twenty-three counts. When this condition exists, the "Q" output of flip-flop 267 is fed over line 268 to inverting buffers 269 and 270 which turns on an indicator 271 and alerts an operator of the system 46 that the laminate 32 has shifted or skewed.

Flip-flops 254, 256, 258 and 267 are identified in the Data Book as MC14013 D-type flip-flop, NAND gates 262, 264 and 266 are identified in the Data Book as MC14011 two-input NAND gate.

Processor Circuit 70

Figure 10:
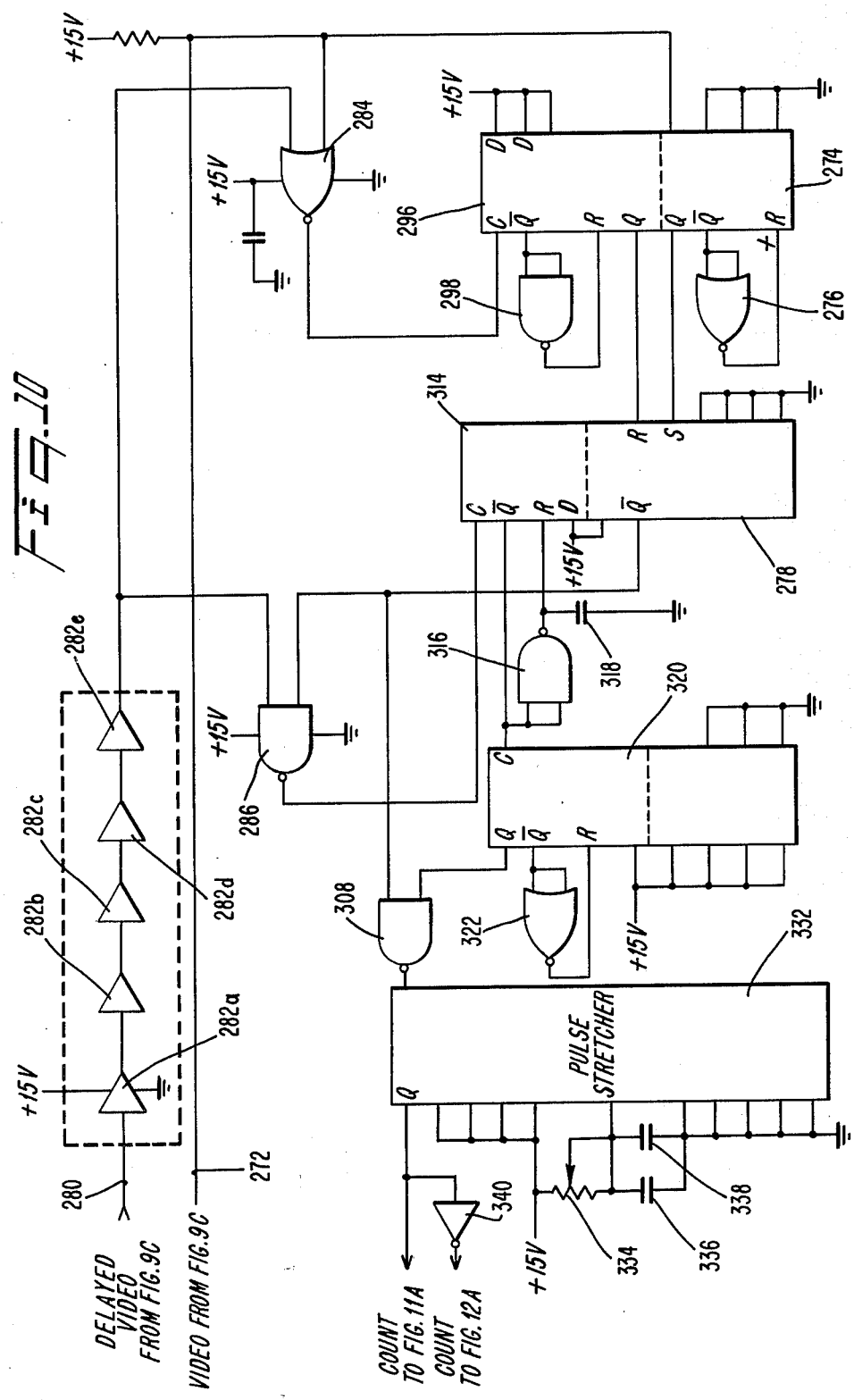
FIG. 10 is a schematic of a processor circuit which receives pulses from the oscillator, timer and threshold adjust system of FIGS. 9A, 9B and 9C and develops an output pulse when a hole count is to be provided in accordance with certain principles of the invention.

Referring to FIG. 10, the video pulse 78a (FIG. 5) is fed from output line 222 (FIG. 9C) to input line 272 of the processor circuit 70. The video pulse is fed to the clock (C) input of a flip-flop 274 to set the flip-flop whereby a positive-going pulse appears at the "Q" output thereof. At the same time, a negative-going pulse appears at the "$\overline{Q}$" output of the flip-flop 274 which is fed through an inverter 276 to the reset (R) input of the flip-flop. This resets the flip-flop 274 whereby the pulse at the "Q" output goes negative. The resultant pulse at the "Q" output is a spike or trigger pulse. The spike pulse is fed to the set (S) input of a flip-flop 278 to set the flip-flop. When the flip-flop 278 is set, a negative-going pulse appears at the "$\overline{Q}$" output of the flip-flop.

The flip-flops 274 and 278 each form one half of a dual type identified in the Data Book as MC14013 dual type flip-flop. The inverter 276 is identified in the Data Book as an MC14001 quad 2-input "NOR" gate.

The delayed video signal is fed from output line 224 (FIG. 9C) to input line 280 of the processor circuit 70.

The delayed video signal is fed through five series-connected, non-inverting buffers 282a–282e which provide slight additional delay to insure that the delayed video pulse is delayed for a period at least equal to the time of one scan cycle. The buffers 282a–282e are identified in the Data Book as MC14050 non-inverting hex buffers. The output of buffer 282e is fed to one input of a NOR gate 284 and one input of a NAND gate 286.

The video pulses, for example pulse 78a, are also fed directly to another input of the NOR gate 284 where output pulses of the gate, for example pulse 288, are represented in FIG. 5 as inverted versions of the input pulses. Referring further to FIG. 5, when the video pulse 78a is fed to the NOR gate 284, there is no delayed video pulse. Consequently, output pulse 288 of NOR gate 284 will be an inverted version of pulse 78a. When the video pulse 80a and delayed video pulse 78b are fed to NOR gate 284, pulse 80a encompasses pulse 78b and the resulting output of the NOR gate is pulse 290. In a similar fashion, pulse 292 appears at the output of NOR gate 284 when pulses 80b and 82a are applied to the gate. When delayed video pulse 82b occurs, there is no pulse appearing at the output 222 because no light was sensed during the scan of line 84 (FIG. 4) as previously described. Therefore, pulse 82b is the only input to NOR gate 284 at this time and the output of the gate is pulse 294 which is an inverted version of pulse 82b.

NOR gate 284 is of the same type as NOR gate 276. NAND gate 286 is identified in the Data Book as an MC14011 quad 2-input NAND gate.

The negative pulses 288, 290, 292 and 294 of NOR gate 284 are fed to the clock (C) input of a flip-flop 296 which is of the same type as flip-flop 274. However, flip-flop 296 will not be set until there is a positive-going transition in the pulse being applied thereto. For example, when pulse 292 (FIG. 5) is at its trailing edge and is therefore positive-going, flip-flop 296 is set and a positive-going pulse appears on the "Q" thereof. At the same time, a negative-going pulse appears on the "$\overline{Q}$" output of flip-flop 296 and is fed through an inverter 298 to the reset (R) input of the flip-flop to reset the flip-flop. The inverter 298 is identified in the Data Book as MC14011 quad 2-input NAND gate. At this time, the "Q" output of the flip-flop 296 goes negative and a positive-going spike or trigger pulse is developed. The spike pulse is fed to the reset (R) input of flip-flop 278 to reset the flip-flop whereby the "Q" output goes positive. Thus the setting of flip-flop 278 by the leading edge of the video pulses through flip-flop 274, and the resetting of flip-flop 278 by the trailing edge of the output pulse of NOR gate 284 through flip-flop 274, results in negative pulses, 300, 302 and 304 (FIG. 5) appearing at the "Q" output of flip-flop 278.

Referring to FIG. 5, the leading edge of video pulse 78a results in the formation of the leading edge of pulse 300 while the trailing edge of pulse 288 of NOR gate 284 results in the trailing edge of pulse 300 to thereby form the negative pulse 300. Negative pulses 302 and 304 are formed in a similar manner. Since there is no pulse occurring at point 84a (FIG. 5) of the video line, flip-flop 274 is not set and consequently flip-flop 278 is not set. Therefore, there is no negative output pulse at point 306 on the output line of flip-flop 274.

Referring again to FIG. 10, as the negative pulses 300, 302 and 304 (FIG. 5) appear at the "Q" output of flip-flop 278, they are fed to the NAND gate 286 and to another NAND gate 308. As noted before, the delayed video pulses 78b, 80b and 82b are also fed to the NAND gate 286. When either input to the NAND gate 286 is negative, the output of the gate will appear positive. When both inputs of the NAND gate 286 are positive, the output will appear negative.

Referring to FIG. 5, the delayed video line is normally at a negative level with positive pulses 78b, 80b and 82b. Thus, the output of NAND gate 286 could only be negative during the occurrence of pulses 78b, 80b and 82b. The pulse line of the "$\overline{Q}$" of flip-flop 278 is normally positive with negative going pulses 300, 302 and 304. Therefore, the output of NAND gate 286 could only be negative during those times when there are no pulses present along the pulse line of the "$\overline{Q}$" of flip-flop 286. This condition occurs for the first time during the occurrence of a leading portion of pulse 80b and immediately before the occurrence of pulse 304. This results in negative pulse 310 which appears at the output of NAND gate 286. The condition occurs again during the occurrence of pulse 82b. At this time, there are no pulses at the "$\overline{Q}$" output of flip-flop 278, represented at point 306 of FIG. 5, whereby the output is positive. The result is a negative pulse 312 at the output of the NAND gate 286.

Referring to FIG. 10, the negative pulses 310 and 312 (FIG. 5) are fed to the clock (C) input of a flip-flop 314 which is set by both negative pulses to provide a negative-going pulse at the "$\overline{Q}$" output thereof. This negative-going pulse is fed through an inverting NAND gate 136 to the reset (R) input of flip-flop 314 to reset the flip-flop. A capacitor 318 is connected between the output of the NAND gate 316 and ground to provide a delay in the resetting of the flip-flop 314. This results in a pulse of short duration which appears at the "$\overline{Q}$" output of flip-flop 314 and is fed to the clock (C) input of a flip-flop 320 to set the flip-flop. NAND gate 308 and inverter 316 are of the type identified in the Data Book as MC14011 quad 2-input NAND gate. Flip-flops 314 and 320 are of the same type as flip-flop 274.

When flip-flop 320 is set, a positive-going pulse appears at the "Q" output and a negative-going pulse appears at the "$\overline{Q}$" output. The negative going pulse is fed through an inverter 322, which is the same type as inverter 276, to the reset (R) input of flip-flop 320 to reset the flip-flop. This results in a positive going spike 324 (FIG. 5) at the "Q" output of flip-flop 320 which is fed to one input of NAND gate 308. Both inputs to NAND gate 308 must be positive before a pulse appears at the output of the gate. Anytime the negative pulses 300, 302 and 304 are fed to the NAND gate 308, the pulses inhibit the gate from providing an output pulse.

Referring to FIG. 5, when positive spike 324 is fed to NAND gate 308, negative pulse 304 is also being fed to the gate thus inhibiting the gate from providing an output as represented at point 326 on the pulse line for the output of the gate. The delay provided by the capacitor 318 delays the development of the positive spike outputs, such as spike 324, of the "$\overline{Q}$" output of flip-flop 320 to insure that the spikes occur simultaneously with the negative-going pulses of the "$\overline{Q}$" output of flip-flop 278 should there be such an output.

When spike 328, which is generated in the same manner as spike 324, appears at the "Q" output of flip-flop 320 and is coupled to NAND gate 308, the "$\overline{Q}$" output of flip-flop 278 is positive as indicated at point 306 on the pulse line in FIG. 5. Since both inputs to NAND gate 308 are positive, a negative count pulse 330 (FIG. 5) appears at the output of the gate and represents the counting of hole 40a (FIG. 4). Note that during the time when count pulse 330 is occurring, there is no video pulse. Thus, the counting of hole 40a (FIG. 4) actually occurs during the time of scan line 84 which is the first scan line on which a "no-light" condition occurs after light was sensed on at least the immediately previous scan line, for example, scan line 82. By use of the delay-and-compare technique employed by the processor circuit 70 and the system 46, whereby preceding video pulses generated in response to a given hole are delayed and compared with the time frame for the next incoming video pulse generated by the same hole, only one count pulse 330 is generated for each hole regardless of the number of times light is sensed over successive scan lines for the same hole.

The count pulse 330 is fed to a pulse stretcher 332 which is identified in the Data Book as an MC14528 multivibrator. A potentiometer 334 and parallel capacitors 336 and 338 are connected to the pulse stretcher 332 and provide an RC time constant which establishes the pulse width of the count pulses appearing at the "Q" output thereof. The "Q" output is fed to (1) the counter reset 68 (FIG. 11A) and (2) the counter-comparator circuit 88 (FIG. 12A) through inverting buffer 340. The inverting buffer 340 is identified in the Data Book as MC14049 hex inverting buffer.

Counter Reset Circuit 68

Referring to FIG. 1, the laminate 32 is formed with many holes 40a and 40b, which give the appearance of a random array of holes. However, each circuit code has an ultimate definitive pattern which is undetectable when the laminate 32 appears as illustrated in FIG. 1. Since each circuit section of the laminate 32 extends twelve inches along the length of 550 feet of the laminate, it would seem logical to begin each counting cycle at a point where each circuit begins. In some instances, many of the holes 40a, 40b and 40c, and the slots 42a and 42b, are located near or at the beginning of a twelve-inch circuit section in some codes. As the laminate 32 is moved adjacent to the scan area, it may shift from side-to-side or become skewed. Under these conditions, it is sometimes difficult to initiate a counting cycle precisely at the beginning of each twelve-inch circuit section which will ultimately form a flexible printed circuit section which will ultimately form a flexible printed circuit. For example, if the trailing holes of one section are very close to the termination of that section and the section is skewed adjacent to the scan area, the trailing holes could be counted as leading holes in the next successive section. As a result, the system 46 would indicate a hole error in both sections. Thus, it would be desirable to start and complete the count cycle by scanning an area which did not contain any holes.

The counter reset circuit 68 provides facilities for selecting the starting point of a twelve-inch counting cycle by setting the start point a specified distance from one of the tool holes 40c or one of the X-slots 42a and in an area containing no holes. In this manner, each count cycle would begin with a first scan line at the same position on each circuit section and, if desired, the position could be other than the origin of the twelve-inch section which will form a printed circuit. Such a count cycle would extend a distance of twelve inches before reading a comparison of actual and preset counts and before beginning the next successive count cycle.

Initially, the repetitive pattern of each given circuit code to be manufactured is examined to determine whether there are any side-to-side clear areas which do not contain any holes. Typically, such areas may be located a distance from the actual origin of the circuit section and measurable by a specified number of tool holes 40c from the X-slot 42a. Otherwise, each circuit section to be examined may contain a given number of tool holes 40c between such successive clear areas. This data is then compiled and made available to an operator as each code is to be manufactured. The data, as provided to an operator in preparation for the manufacture of a selected code, will instruct the operator to either base the count-cycle starting point on an "X SLOT" or a "TOOL HOLE" option.

Referring to FIG. 11A, if the "X SLOT" option is selected, a manually operable, single-pole double-throw switch 342 is set to a "X SLOT" position which connects the switch to positive fifteen volts. Then, in accordance with the data, the operator may be instructed to start the count cycle a given number of tool holes 40c after the X-slot 42a, whereby an adjustment is made to a BCD thumb wheel switch 344 to preset the number of tool holes to be counted.

If the operator is instructed to use the number of tool hole 40c within each circuit section to be examined to establish the starting point for each counting cycle, the switch 342 is set to a "TOOL HOLE" position which connects the switch to ground potential. The switch 344 is then set to the number of tool holes 40c in each circuit section.

Assume that a holeless clear area has been located and is repeated every twelve inches. Also assume that there are three tool holes 40c located between successive clear areas and that other holes 40a and 40b remain to be counted between the scan line of the third tool hole 40c and the next clear area.

Initially, the "TOOL HOLE" option has been selected and, as noted before, there are three tool holes 40c within each of the successive circuit sections of repetitive patterns to be examined. The operator is instructed to position the switch 342 in the "TOOL HOLE" position and set the BCD switch 344 to a count of three. Referring to FIG. 13, the upperside of a section of the laminate 32 is illustrated and contains one tool hole 40c, one X-slot 42a and one hole 40a. The light beam 50 is directed through the lens 54 having end portions which extend from opposite sides of the laminate 32. As noted above, the laminate 32 may shift or skew whereby the edge of the laminate moves laterally relative to the width of the lens 54. Since each tool hole 40c and X-slot 42a is always a known distance from the adjacent edge of the laminate 32, it is important within the counter reset circuit 68 to know when the left edge of the laminate, as viewed in FIG. 13, appears during each scan cycle in order to establish a consistent point of reference between successive scans regardless of shifting or skewing of the laminate.

As shown on the "video" line of FIG. 13, the system 46 is in a start mode before light is sensed at portion 54a of the lens 54. During the start mode, the video line is negative at location 346. When light is sensed at portion 54a, the positive pulse 232 is developed. When the left edge of the laminate 32 is scanned, the "video" line goes negative until tool hole 40c is reached. At that time a positive pulse 350 is developed. Ultimately, pulse 352, representing the appearance of the X-slot 42a, and pulse 354, representing portion 54b of the lens 54 are developed. Since hole 40a, as illustrated in FIG. 13, does not fall on any scan line coincident with any scan line of the tool hole 40c and X-slot 42a, pulse 356 will not be developed during this scan cycle. However, pulse 356 is illustrated in phantom to show that it will appear on a "video" line when the hole 40a is scanned during another cycle.

Figures 11, 11C:
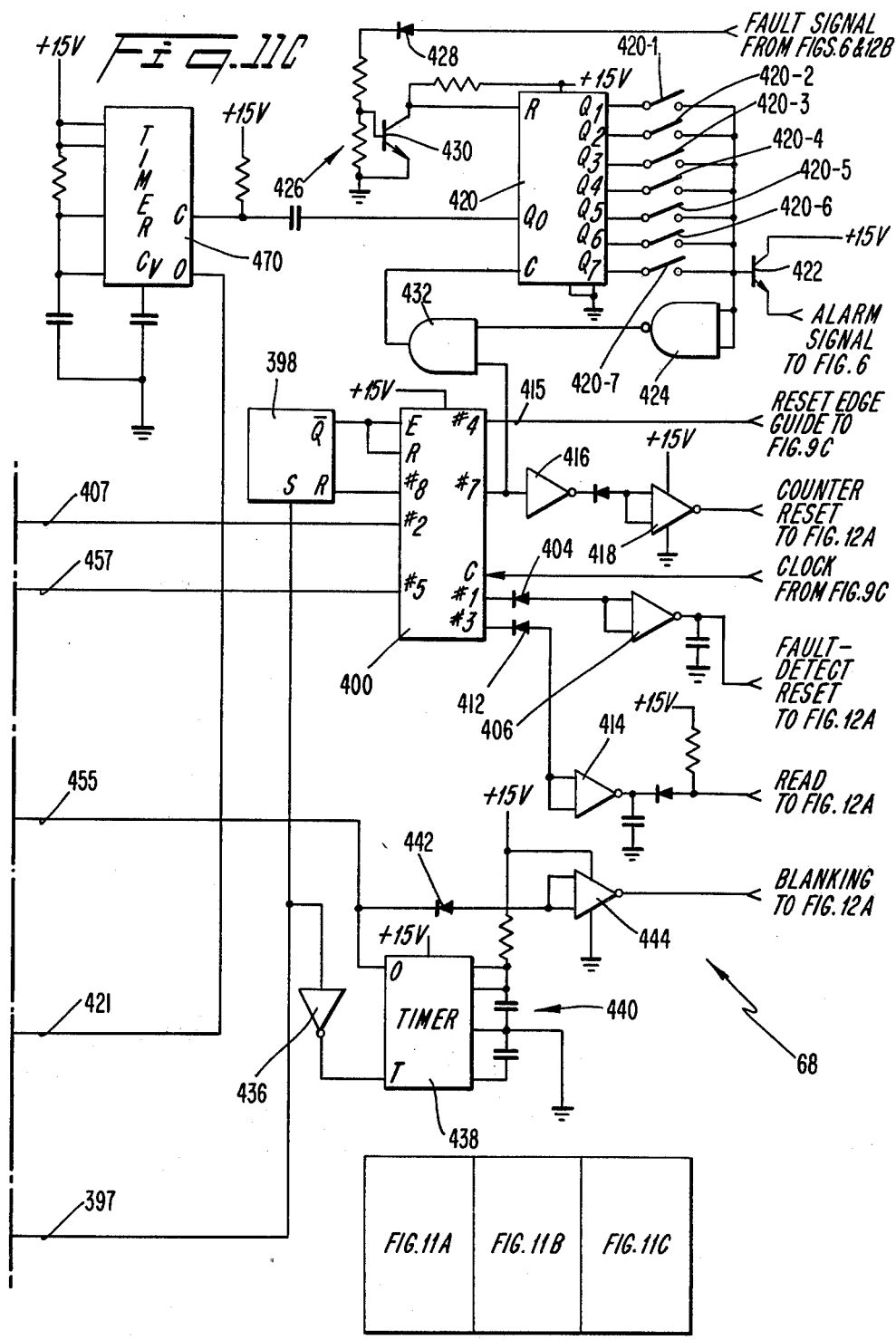
Figure 11B:
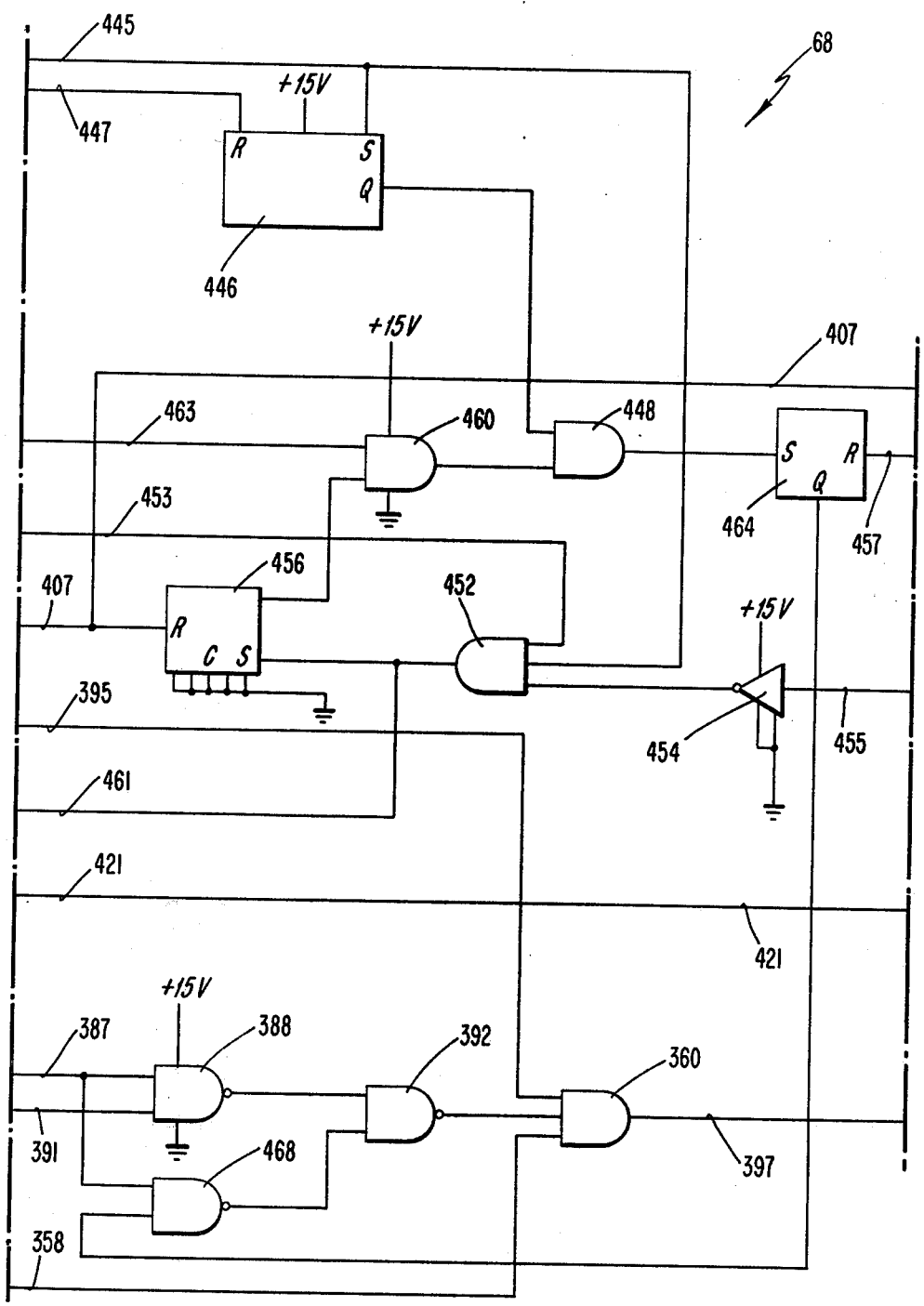

During the start mode when the "video" line is negative at location 346, the system 66 (FIGS. 9A, 9B and 9C) in combination with the start photocell circuit 51 (FIG. 7) develops the sync pulse 234. Referring to FIGS. 11A, 11B and 11C, the sync pulse 234 is fed from output line 238 (FIG. 9C) to input line 358. The sync pulse 234 is further fed to an input of "AND" gate 360 (FIG. 11B).

Count-twenty-three pulse 250 is fed from the shift register 240 (FIG. 9A) to the set (S) input of a flip-flop 364 while count-forty pulse 251 is fed to the reset (R) input of the flip-flop to reset the flip-flop. This results in the development of a tool-hole-window pulse 368 (FIG. 13) appearing at the "Q" output of flip-flop 364 which is fed to the data (D) input of a normally set flip-flop 370. The tool-hole window represents the period of time during which the tool hole 40c should be present during the scan cycle and is based on a time measurement extending between the twenty-third and fortieth clock pulses of the shift register 240 (FIGS. 9A, 9B and 9C) as measured from the edge of the laminate 32.

The "Q" output of flip-flop 370 is coupled to a BCD counter 372 which is further coupled to a comparator 374. The preset tool hole count of the BCD switch 344 is also fed to the comparator 374 whereat the actual and preset counts are compared. The output of the comparator 374 is fed through an inverting buffer 376 to an input of AND gate 378. There is no signal appearing on the output of the comparator 374 if the preset and actual counts are not equivalent. Thus, the inverting buffer 376 presents a high signal on the input of AND gate 378. Count-twenty-three pulse 362 is fed to the AND gate 378 which also receives the video signal developed in the system 66 (FIG. 9C). This results in a positive pulse being fed to the reset (R) input of the flip-flop 370 whereby the flip-flop is reset. When flip-flop 370 is reset, the "Q" output goes negative and the "Q̄" output goes positive which is fed to one input of an AND gate 380. When the tool hole 40c is counted in the manner previously described, the count pulse is fed from the processor circuit 70 (FIG. 10) to the other input of the AND gate 380 whereby a positive pulse is fed through an inverting buffer 382 to the clock (C) input of flip-flop 370. Since both the data (D) and clock (C) input of the flip-flop 370 are now positive, the flip-flop is returned to its normally set condition whereby the "Q" output goes positive. This results in the development of a tool-hole-found pulse 384 which represents that the tool hole 40c is coincident with and was located during the time the tool-hole-window pulse 368 and is, therefore, the tool hole to be counted rather than another one of the many holes in the laminate 32.

The tool-hole-found pulse 384 is fed to the BCD counter 372 which further feeds the comparator 374. The light beam 50 continues to scan the moving laminate 32 and the system 46 counts the holes 40a, 40b and 40c, and the slots 42a and 42b, as previously described. When the third tool hole 40c within the circuit section under examination is counted, the comparator 374 makes a favorable comparison between the actual and preset counts and feeds a positive output pulse 386 (FIG. 13) to the buffer 376 and over line 387 to an input of a NAND gate 388. When the switch 342 is placed in the "TOOL HOLE" option, ground or a low potential is applied to an inverter 390 which provides a positive output. The positive output is fed over line 391 to the other input of NAND gate 388 whereby the output of NAND gate 388 is negative. The negative output of NAND gate 388 is fed to a NAND gate 392 which feeds a positive input to the AND gate 360 which will be retained on the input of the AND gate until the counter 372 is reset.

The video and edge pulses, developed in the system 66 (FIGS. 9A, 9B and 9C) are fed to the clock (C) input and the reset (R) input of a counter 394, respectively. Counter 394 receives and counts incoming video pulses but will provide a positive output only when the first incoming video pulse of each scan cycle is counted. This output must be coincident with the sync pulse 234 (FIG. 13) and occur after the counting of the third tool hole 40c in order for an output to be developed on the AND gate 360. Since counter 394 is reset during each scan cycle by pulse 248 (FIG. 13), which represents the edge of the laminate 32, the counter will count all video pulses occurring thereafter. As noted previously, there are additional holes 40a and 40b to be counted after the third tool hole 40c has been counted but before the clear area of no holes has been reached. Consequently, upon the occurrence of the video pulse of the first hole 40a or 40b on each scan line between the tool hole 40c and the holeless clear area, a positive pulse appears at the output of the counter 394 and is fed over line 395 to the AND gate 360. However, these video pulses of the first holes on each scan line do not occur simultaneously with the sync pulse 234. Therefore, the output of AND gate 360 remains negative.

When the holeless clear area is first reached after the third tool hole 40c has been counted, the first time that light is sensed during the scan cycle is when the scan passes over the right edge of the laminate (FIG. 13) and senses the light emanating through portion 54b of the lens 54. This results in the development of video pulse 354 (FIG. 13) which is fed to the counter 394 to provide a positive count-one pulse 396 (FIG. 13) at the count-one output thereof. Pulse 396, as illustrated in FIG. 13, begins at the right side of the figure but continues on sync at the left side until light is sensed again at portion 54a of the lens 54. Counter 394 then counts the second video pulse 348, which results from the light emanating from portion 54a of lens 54, and the output moves to the count-two output of the counter which is not connected to any external circuit. Since no output pulse appears on the count-one output of counter 394, the pulse 396 terminates and the output goes negative as illustrated in FIG. 13. The negative output at the count-one output of counter 394 is then fed over line 395 to AND gate 360 to inhibit the gate. When the left edge of the laminate 32 is sensed, as viewed in FIG. 13, pulse 248 is developed by flip-flop 244 (FIG. 9C) and resets counter 394 to begin the next scan cycle.

During the period when pulse 396 is appearing at the count-one output of counter 394, the sync pulse 234 (FIG. 13) will occur and all three inputs to AND gate 360 will be positive for the period of the sync pulse whereby the output of the AND gate goes positive. The positive output of the AND gate 360 is fed over line 397 to the set (S) input of a flip-flop 398 which sets the flip-flop.

When the flip-flop 398 is set, the "Q̄" output is fed to a counter 400. The 500 KHz clock signal, which is developed by the system 66 (FIG. 9C), is fed to counter 400. When the "Q̄" output of the set flip-flop 398 is fed to the counter 400, the counter is enabled and begins to count at the 500 KHz frequency. As long as flip-flop 398 remains in the set state, counter 400 will continue to count. This is represented by "enabled" pulse 402 (FIG. 13). When count-one pulse occurs in counter 400, an output is fed through a diode 404 and an inverter 406 to provide the "fault-detect reset" pulse 88c (FIG. 13) to the counter-comparator circuit 88 (FIG. 12B).

When count-two pulse occurs in the counter 400, a positive pulse is fed over line 407 to one input of a NAND gate 408. The other input of NAND gate 408 is already positive by virtue of the positive output of NAND gate 390. The output of NAND gate 408 then goes negative and is fed to a NAND gate 410. The output of NAND gate 410 goes positive and is fed to the reset (R) input of the BCD counter 372 to reset the counter. The output of the comparator 374 then goes negative and the outputs of AND gates 360 and 378, and NAND gates 388 and 392 are reversed. Since flip-flop 398 has been set, it remains in this state and counter 400 thereby remains enabled to continue counting.

When count-three pulse of counter 400 occurs, an output is fed through a diode 412 and an inverting buffer 414 to provide the "read" pulse 88a (FIG. 12) to the counter-comparator circuit 88 (FIG. 11).

When count-four pulse of counter 400 occurs, an output is fed over line 415 to a reset (R) input of flip-flop 267 (FIG. 9C) to provide an "edge fault reset" pulse to the system 66 (FIGS. 9A, 9B and 9C).

When count-seven pulse of the counter 400 occurs, an output is fed through inverting buffers 416 and 418 to provide the "counter reset" pulse 88b (FIG. 13) which is fed to the counter-comparator circuit 88 (FIG. 11).

As previously described, the system 46 examines successive circuit sections of the laminate 32 to determine whether there are any holes missing in any circuit section. If one or more holes are missing in any circuit section, the system 46 provides visual indication that the circuit section has failed. If a selected number of successive circuit sections fail, it is imperative that the operator be made aware of the successive failures. Also, it is desirable to stop the punch press 44 at this time. In order to facilitate a warning to the operator, seven outputs of a counter 420 are connected to seven switches 420-1 through 420-7. The switches 420-1 through 420-7 are each connected to the base of a transistor 422 and the input of an inverter 424.

The number of successive circuit-section failures which will require operator attention and shutdown of the punch press 44 is selectable by closure of any one of the switches 420-1 through 420-7. For example, if the failure threshold is three successive circuit-section failures, switch 420-3 is closed while all other switches remain open.

It is noted that successive failures are indicative of a continuing problem such as damaged, missing or worn punches and can not be tolerated. Therefore, the notification of such failure is imperative. Failures which are not successive up to the selected number and which occur infrequently can be tolerated. Thus, notification of such infrequent failures is not required.

A level-sensing circuit, designated generally by the numeral 426 (FIG. 11C), includes a diode 428 and a transistor 430. When a circuit section contains all the required holes, ground is fed from the counter-comparator circuit 88 (FIG. 12B) to the input of circuit 426 at diode 428. This provides a potential difference across the diode 428 of zero volts which is insufficient to cause the diode to conduct. Thus the base of transistor 430 is at zero volts and the transistor will not conduct. Since transistor 430 is not conducting, the reset (R) input of counter 420 is at a positive fifteen volts which holds the counter 420 in the reset mode.

When a defective circuit section is examined, a fault signal at positive five volts is fed from the counter-comparator circuit 88 (FIG. 12B) and supplied to the input of circuit 426 at the diode 428. Thus, five volts is now applied across the diode 428 which causes the diode to conduct. When this occurs, the base of the transistor 430 is biased sufficiently to cause the transistor to conduct. This places zero volts at the reset (R) input of counter 420 to prevent the counter from going into the reset mode.

Regardless of the mode of the counter 420, when count-seven pulse occurs in counter 400, a positive pulse is fed to the input of an AND gate 432 with the other input thereof normally positive. The output of AND gate 432 goes positive and is fed to the clock (C) input of the counter 420 to register one count within the counter. If the circuit section which has just been examined contains all required holes, counter 420 is in the reset mode as described before. Therefore, the input of the positive pulse at the clock (C) input of counter 420 has no effect on the counter.

If the circuit section has failed, the counter 420 is not in the reset mode and one count is registered in the counter when the positive pulse is fed from AND gate 432 to the counter. If the next circuit section contains the required number of holes, circuit 426 responds and facilitates the resetting of counter 420 whereby the registered one count is erased. However, if three successive circuit sections fail, three counts are registered in counter 420 whereby a positive pulse is fed through switch 420-3 to the base of transistor 422 whereby the transistor conducts. An alarm signal, which is a positive pulse, is then fed to the alarm circuit 92 (FIGS. 2 and 6). The positive pulse is also fed to the inverter 424 which feeds a negative pulse to the AND gate 432. This inhibits AND gate 432 and prevents subsequent positive pulses from being fed from the AND gate to the counter 420. Thus, the counter 420 is locked at the three counts whereby the alarm signal continues to operate to insure that the operator is apprised of the three successive failures.

When count-eight pulse of counter 400 occurs, an output pulse 434 (FIG. 12) is fed to the reset (R) input of flip-flop 398 to reset the flip-flop which turns off the counter.

Figure 12A:
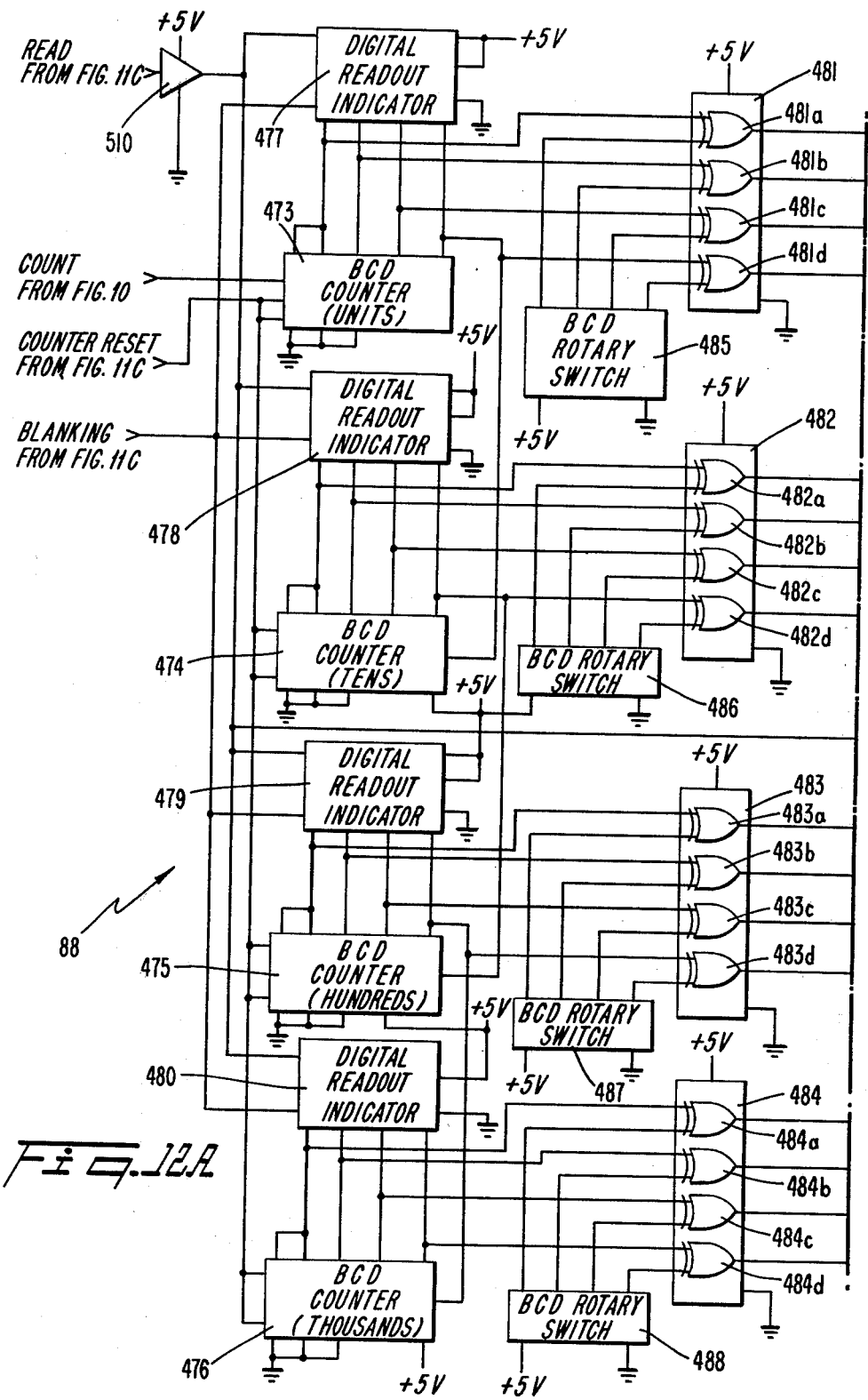

During the period when the positive output of gate 360 is fed over line 397 to the flip-flop 398, it is also fed through an inverting buffer 436 to a timer 438 to start the timer. The output of the timer 438 is a positive pulse of extended width when compared with the width of output pulses from counter 400. The width of the output pulse of the timer 438 is determined by an RC network 440. The output of the timer 438 is fed through a diode 442 and an inverting buffer 444 to provide "blanking" pulse 88d (FIG. 13). "Blanking" pulse 88d is fed to the counter-comparator circuit 88 (FIG. 12A).

When the "TOOL HOLE" option is selected in the manner described above, the counter reset circuit 68 responds to various input pulses at precise times during the examination of each circuit section and provides output pulses. These output pulses, which are developed at the conclusion of the examination of each circuit section, include the "read" pulse 88a, "counter reset" pulse 88b, "fault-detect reset" pulse 88c, and the "blanking" pulse 88d. The circuit 68 also provides a single count pulse to counter 420 for each circuit section examined and an output alarm signal if a preset number of successive section failures has been reached.

Assume now that the operator has been instructed to select the "X SLOT" option and that a holeless clear area appears between the fourth and fifth tool hole 40c beyond the X-slot 42a. It is noted that the clear area may be some distance from the X-slot 42a but the X-slot can be used as a point of reference on each circuit section to facilitate location of the clear area.

Referring to FIG. 11A, the operator will place switch 342 in the "X SLOT" position and set thumbwheel switch 344 to a count of four. This places a positive fifteen volts at the input of inverter 390. The output of inverter 390 goes negative and thereby inhibits NAND gates 360 and 408.

Count-forty-four pulse 252 (FIG. 13) is fed over line 445 (FIGS. 11A and 11B) from the system 66 (FIG. 9C) to the set (S) input of a flip-flop 446 (FIG. 11B) to set the flip-flop. The "Q" output of flip-flop 446 goes positive which is fed to one input of an AND gate 448. When count-sixty-two pulse 253 (FIG. 13) occurs, which is fed over line 447 (FIGS. 11A and 11B), flip-flop 446 is reset whereby the "Q" output goes negative and AND gate 448 is inhibited. During the period when flip-flop 446 is in the set mode, a positive pulse 450 (FIG. 13) appears at the "Q" output and represents an X-slot window during which the X-slot 42a should occur.

The count-forty-four pulse 252 is also fed to an AND gate 452 along with the video signal which is fed over line 453 and the output of the timer 438, which is fed through inverting buffer 454 over line 455. Since the X-slot-window pulse 450 (FIG. 13) was established to represent the time frame when an X-slot video pulse should occur, the output of AND gate 452 will go positive when pulse 450, X-slot video pulse 352 and the output of the timer 438 occur simultaneously. Thus, the positive output from AND gate 452 is fed to the set (S) input of a flip-flop 456 to set the flip-flop. At this time, the "Q" output of flip-flop 456 goes positive as illustrated by pulse 458 (FIG. 13) and represents that the X-slot 42a has been located. The positive "Q" output of flip-flop 456 is fed to an AND gate 460.

When AND gate 452 goes positive, this output is also fed over line 461 to an input of a NAND gate 462. The other input of NAND gate 462 is already positive through the "X SLOT" option of switch 342. When both inputs of NAND gate 462 are positive, the output goes negative which is fed to NAND gate 410. The output of NAND gate 410 then goes positive which is fed to the reset (R) input of BCD counter 372 to reset the counter to zero in preparation for counting four holes now that the X-slot 42a has been located.

When X-slot 42a is counted, a count-pulse, which is developed by the processor circuit 70 (FIG. 10), is fed over line 463 to the other input of AND gate 460 whereby both inputs are now positive and the output goes positive. The positive output of AND gate 460 is fed to AND gate 448 whereby both inputs are now positive and the output goes positive. The positive output of AND gate 448 is fed to the set (S) input of a flip-flop 464 which is thereby set. Even though the positive inputs to AND gates 448 and 460 may now be removed, flip-flop 464 remains in the set mode. When flip-flop 464 is in the set mode, the "Q" output is positive as illustrated by pulse 466 (FIG. 13). Pulse 466 represents that X-Slot 42a has now been counted and the counting of the four succeeding tool holes 40c can begin.

The positive "Q" output of flip-flop 464 is fed to one input of a NAND gate 468. The tool holes 40c eventually pass the light beam 50 and are detected and counted. The counter reset circuit 68 processes the tool-hole pulses in the same manner as previously described whereby two hole counts are fed to and stored in the BCD counter 372. When the actual tool hole count in the counter 372 is equal to the count which is preset in the thumbwheel switch 344, the output of comparator 374 goes positive and is fed to NAND gate 468. The output of NAND gate 468 goes negative and is fed to NAND 392 which provides a positive output. The positive output is fed to one of the inputs to AND gate 360. This input to AND gate 360 will remain positive as long as the output of the comparator 374 and the "Q" output of flip-flop 464 remain positive.

When the holeless clear area is reached, video pulse 354 (FIG. 13) occurs and is fed to counter 394 whereby pulse 396 (FIG. 13) appears at the count-one output of the counter. When the next sync pulse 234 (FIG. 13) occurs, all inputs of AND gate 360 are positive and the output goes positive. The positive output of AND gate 360 is fed to the set (S) input of flip-flop 398 to set the flip-flop.

When the flip-flop 398 is set, counter 400 is enabled as previously described and proceeds through the counting cycle to provide the various output pulses to the counter-comparator circuit 88 (FIGS. 12A and 12B). When count-two pulse occurs in counter 400, a positive pulse is fed over line 407 to the reset (R) input of flip-flop 456 to reset the flip-flop. When count-five pulse in counter 400 occurs, a positive pulse is fed over line 457 to the reset (R) input of flip-flop 464 to reset the flip-flop. A count pulse is also fed to counter 420 in the same manner previously described. Also, the timer 430 is started to provide the "blanking" pulse 88d (FIG. 12).

The "$Q_o$" output of the counter 420 is fed to the clock (input) of a timer 470 whereby a positive pulse appears on the output of the timer. The positive output is fed over line 421 to the clock (C) input of the counter 372 and facilitates an additional count within the counter. When the "$Q_o$" output goes positive, an error has been detected. This error could be caused by the system 46 scanning one half of one circuit section and one half of the succeeding circuit section, thus causing an erroneous hole count. The timer 470 facilitates shifting the start of the next scan cycle by a distance of one tool hole. This shifting of the scan cycle only occurs on the first error condition detected by the counter 420.

Thus, when the "X SLOT" option is selected, the counter reset circuit 68 operates in a manner similar to the operation during the "TOOL HOLE" option except that the point of starting the operation depends on the sensing and counting of the X-slot 42a before counting the tool holes 40c.

The buffers 406, 414, 418 and 444 are of a type identified as a Dual Buffer type 932 manufactured by Fairchild Semiconductor. The timers 438 and 470 are manufactured by Fairchild Semiconductor as their type uA556. The thumbwheel switch 344 is manufactured by Digitran Company of Pasadena, California, as their Model 311-1.

The following information identifies the remaining major components of the counter rest circuit 68 and are all listed in the Data Book. The flip-flops 364, 370, 398, 446, 456 and 464 are identified as type MC14013. The buffers 376, 382, 416, 436 and 454 are identified as types MC14049. The NAND gates 388, 390, 392, 408, 410, 424, 462 and 468 are identified as type MC14011. The counters 394, 400 and 420 are identified as type MC14017 and the counter 372 as type MC14518. The comparator is identified as type MC14585. The AND gates 360, 378 and 452 are identified as type MC14073 and AND gates 380, 432, 448 and 460 as type MC14081.

Counter-Comparator Circuit 88

Referring to FIGS. 12A and 12B, the counter-comparator circuit 88 includes a counter portion 472. The counter portion 472 includes four binary-coded-decimal (BCD) counters 473-476 which are connected in series to count any number from 0 through 9999. The counters 473-476 function as units, tens, hundreds and thousand counters, respectively, and are manufactured by Motorola, Incorporated as their type MC7490. The outputs of the four counters 473-476 are connected to four digital-readout indicators 477-480, respectively, which are manufactured by Dialight Company of Brooklyn, New York as their Model 749-0904. The output of the counter 473-476 are also connected to four comparators 481-484, respectively. Four BCD rotary switches 485-488 have outputs also connected to thr four comparators 481-484, respectively. The switches are manufactured by Digitran Company as their Model 311-4.

Each of the comparators 481-484 includes four exclusive OR gates which are identified with each comparator number and the letters a-d. The exclusive OR gates are manufactured by Motorola, Incorporated, as their type MC7486. The outputs of the comparators 481 and 482 are fed to an NAND gate 490 while the outputs of the comparators 483 are fed to a NAND gate 492. The outputs of the NAND gates 490 and 492 are fed through two inverting buffers 494 and 496, respectively, and into a NAND gate 498. The NAND gates 490 and 492 are manufactured by Motorola, Incorporated as their type MC7430. The inverting buffers 494 and 496 are manufactured by Fairchild Semiconductor as their type 936. The NAND gate 498 is also manufactured by Fairchild Semiconductor as their type 962.

The output of the NAND gate 498 is normally positive and is fed to the set (S) input of a flip-flop 500 which normally produces a negative "$\overline{Q}$" output is fed to the base of a transistor 502 to bias the transistor into a nonconducting state. This prevents the connecting of ground to a red "failure" lamp 504. The flip-flop 500 is manufactured by Motorola, Incorporated, as their type MC7470.

The positive "Q" output of the flip-flop 500 is fed to the base of a transistor 506 to bias the transistor into conduction. When transistor 504 is conducting, ground is applied to a green "pass" lamp 508 whereby the lamp is illuminated. Thus, the green lamp 508 remains illuminated during normal operation of system 46 while the red lamp 504 is not illuminated.

Prior to the passing of the laminate 32 (FIG. 1) through the scanning area, an operator reviews the code requirements and determines the total number of holes 40a, 40b and 40c, and slots 42a and 42b that should be formed in each circuit section of the laminate. The operator then sets this hole count into the four rotary-switches 485-488. This is a preset count which is to be compared with the actual count of holes and slots in the laminate 32. The rotary switches 485-488 are provided with visual read-out displays to show the preset count.

As the laminate 32 is moved past the scanning area, the light beam 50 scans the moving laminate whereby an actual count of the holes 40a, 40b, 40c and slots 42a and 42b is made in the manner described hereinbefore. This actual count is fed from the output of the buffer 340 (FIG. 10) into the units counter 473. As the count progresses, it may be shifted to the tens, hundreds and thousands counters 474-476, respectively, depending on the number of holes and slots being counted. The outputs of counter 473-476 are continuously being fed to respective indicators 477-480. However, the indicators 477-480 are not registering, for readout, the incoming count pulses but are retaining the total count registered for the most recent complete circuit section examined by the light beam 50.

The outputs of the counters 473-476, which are fed to the comparators 481-484, respectively, are compared therein with the present preset count of the switches 485-488. Assuming the correct number of holes and slots appear in the laminate 32 and have been counted, each of the exlusive OR gates of the comparators 481-484 will provide a positive output. These positive outputs are then fed to the respective NAND gates 490 and 492 whereby the normally positive outputs of the NAND gates 490 and 492 go negative. The negative outputs of NAND gates 490 and 492 are inverted by buffers 494 and 496, respectively, and the positive outputs thereof are fed to two inputs of the NAND gate 498.

At this time, the "fault-detect reset" pulse 88c (FIG. 13) is fed from the counter reset circuit 68 (FIG. 11C) to the reset (R) input of the flip-flop 500 to reset the flip-flop. The "$\overline{Q}$" output then goes positive and the "Q" output goes negative whereby transistor 506 is rendered nonconducting and the green lamp 508 starts to go off and transistor 502 is rendered conductive and the red lamp 504 starts to be illuminated.

An instant after the "fault-detect reset" pulse 88c has completed its cycle, the "read" pulse 88a fed from the counter reset circuit 68 to an inverting buffer 510, of the same type as buffer 494. The output of the buffer 510 is a positive pulse which is fed to the indicators 477-480 whereby the indicators display the actual count stored in the counters 473-476 which can be visually compared with the readout of the preset rotary switches 485-488 if desired. The positive pulse output of the buffer 510 is also fed to the remaining input of the NAND gate 498. Since positive pulses appear on the remaining two inputs to the NAND gate 498 due to the favorable comparison of the actual and preset counts, a negative output appears at the output of the NAND gate for the period of the "read" pulse 88a. When the "read" pulse 88a ceases, the output of the NAND gate 498 goes positive whereby the flip-flop 500 is again set to provide illumination of the green lamp 508 and the extinguishing of the red lamp 504.

Due to the close occurrence of the "fault-detect reset" pulse 88c and the "read" pulse 88a, the filaments of the red lamp 504 are not sufficiently heated for illumination before flip-flop 500 is again set. Similarly, the filaments of the green lamp 508 are not sufficiently cooled to extinguish the lamp. Therefore, due to the rapid resetting and setting of flip-flop 500 when a favorable comparison of actual and preset counts is made, the green "pass" lamp 508 gives the appearance of continuous glow while the red "fail" lamp 504 is not illuminated.

If any number of the holes 40a, 40b and 40c, and slots 42a and 42b are missing, the outputs of some of the comparators 481-484 will be negative where unfavorable comparisons are made. In this instance, one or both of the NAND gates 490 and 492 will be positive which is inverted by the buffers 494 and 496 and then fed to the inputs of NAND gate 498.

As noted before, the "fault-detect reset" pulse 88c is then fed to the reset (R) input of the flip-flop 500 to reset the flip-flop. Again the red lamp 504 starts to become illuminated while the green lamp 508 starts to be extinguished. Soon thereafter, the "read" pulse 88a is fed to the counter-comparator circuit 88 which results in the application of a positive pulse to the remaining input of NAND gate 498. Since either, or both, of the remaining two inputs of NAND gate 498 are negative due to an unfavorable comparison of actual and preset counts, the output of NAND gate 498 remains positive. Since there is no transition at the output of NAND gate 498, the flip-flop 500 is not set. Consequently, due to the resetting of flip-flop 500, the red "failure" lamp 504 is illuminated to indicate a failure and the green lamp 508 is extinguished. Also, a fault signal is fed from the "$\overline{Q}$" output of flip-flop 500 to counter reset circuit 68 (FIG. 11C) to register the failure. If desired, the unfavorable count comparison can be visually observed by the actual count on the digital read-out indicators 477-480 and the preset count on the rotary-switches 485-488.

It is noted that the actual counts are made for each twelve-inch section of the laminate 32 and that the two foregoing "pass" and "failure" examples each represent a twelve-inch circuit section. Further, the system 46 provides a single "failure" indication for any given circuit section that fails regardless of the number of missing holes for that given circuit section.

Since flip-flop 500 was not set during the occurrence of the "read" pulse 88a, the red lamp will remain illuminated during the entire period of counting for the next successive twelve-inch circuit section. Upon completion of the counting, the "fault-detect reset" pulse 88c is again applied to the reset (R) input of flip-flop 500. However, flip-flop 500 is already in the reset mode because it was not set during the previous "read" pulse 88a. Therefore, the red lamp 504 remains illuminated at this time. Then, immediately thereafter, the "read" pulse 88a is fed to the counter-comparator circuit 88. If a favorable count comparison has been made, flip-flop 500 is then set, the red lamp 504 is extinguished and the green lamp 508 is illuminated to indicate the favorable comparison. If the count comparison is unfavorable, the red lamp 504 remains illuminated to indicate the failure and the laminate 32 continues to move to begin the hole counting of the next successive twelve-inch circuit section.

Alarm Circuit 92

When the preset number of successive circuit section failures is reached, the counter 420 (FIG. 11C) provides a positive output through a selected one of the switches 420-1 through 420-7. Transistor 422 then conducts and the positive alarm signal is fed to the alarm circuit 92 (FIGS. 2 and 6).

Referring to FIG. 6, the positive alarm signal from the counter reset circuit 68 (FIG. 11C) is applied to a solid state relay 512 which, when operated, effectively connects together lines 514 and 516. This facilitates the application of 115 volts AC to a flasher 518 and a buzzer 520 as well as a lamp 522 connected across the buzzer. By operation of the flasher 518, the buzzer 520 will provide an intermittent audible sound and the lamp 522 will operate intermittently. This combination will provide a visual and an audible alarm for the operator as indication of the preset number of successive circuit-sections failures.

Operation of the solid state relay 512, also facilitates the application of 115 volts AC to energize a relay coil 524a which opens a relay contact 524b. This disables the punch press 44 by removing the operating control power thus stopping the punching operation.

Since counter 420 (FIG. 11C) has reached the selected count, AND gate 432 has been inhibited by the negative output of NAND gate 424 as previously described. Therefore, the counter 420 is in the count or "set" mode at the preselected count and is held in this mode by the inhibiting of AND gate 432. When it is time to restart the punching operation and the hole counting process, counter 420 must be reset and operating power is to be applied to the punch press 44. This is accomplished by depressing manual switch 526 to facilitate the application of ground to the input of counter 420 whereby the level-sensing circuit 426 is biased to reset the counter. Operation of manual switch 526 also breaks the hold of the coil 524a and permits the contact 524b to reclose whereby operating control power can again be applied to the punch press 44.

While the various components of the system 46 have been identified throughout the DETAILED DESCRIPTION, such identification is by way of example and other compatible components may be used to replace those which have been identified without departing from the spirit and scope of the invention.

In summary, the system 46 scans the moving laminate 32 to count the number of holes 40a, 40b and 40c, and slots 42a and 42b, contained within each of many successive twelve-inch circuit sections in a length of 550 feet of laminate. Due to the minuteness of some holes, the time for each scan cycle must be sufficiently fast to insure that such holes in the moving laminate 32 are scanned at least once. Consequently, the larger holes will be scanned many times whereby light sensed for each hole during each of such scans and several light pulses are developed for the same hole having levels proportional to the amount of light sensed. Therefore, the development of each light pulse can not be used as a hole-count indicator.

The levels of each of the developed light pulses are compared to the preset threshold level established by the threshold adjust circuit 122 and a threshold or video pulse is developed when the light pulse level exceeds the threshold level. The video pulse facilitates the reduction of the threshold level thus allowing levels of light pulses from non-coincident scans to exceed the reduced threshold level and produce a video pulse.

The system 46, within the oscillator, timer and threshold adjust system 66 in combination with the processor circuit 70, delays and, in effect, stores as digital memory each video pulse developed in response to the sensing of a given hole and compares the next video pulse from the given hole with the immediately preceding stored pulse. If a video pulse and a stored pulse are simultaneously present, no hole-count pulse is developed. When the hole has passed the scan area, there is no video pulse for the next scan cycle following the given hole. When the immediately preceding stored pulse is compared with the time frame of the absent-video pulse, this provides indication that the given hole has passed and a single hole-count pulse for the hole is developed.

Thus, where a plurality of successive holes occur along a single scan of the laminate 32, a train of successive video pulses will be developed. Each video pulse will appear in an associated one of successive time frames along the scan with each time frame representing the potential location of an associated one of the holes. The train of video pulses is delayed, and effectively stored as digital memory, for a period of one scan cycle. The train of stored pulses is compared with the corresponding successive time frames on the next succeeding scan of the laminate 32. In each instance where no video pulse occurs in any of the corresponding time frames during comparison with the corresponding stored pulse, a single count pulse is developed. In this manner, every hole appearing in the laminate 32 will be counted.

The hole-count pulses for each circuit section of the laminate 32 are compared with a preset count in the counter-comparator circuit 88 (FIGS. 12A and 12B). If the actual and preset counts compare favorably, visual indication is provided by green lamp 508 (FIG. 12B). If the actual and preset counts do not compare favorably, a visual indication is provided by red lamp 504 (FIG. 12B) which indicates that one circuit section of the laminate 32 had one or more holes missing. This indicates a hole-missing failure in one circuit section but does not indicate the number of missing holes. At the end of each counting cycle, indicators 477–480 (FIG. 12A) provide a readout of the actual number of holes counted during the counting cycle. If desired, visual comparison can be made with the preset count displayed in the BCD rotary switches 485–488.

Facilities are provided for presetting, within the system 46, the number of unacceptable successive circuit-section failures and, when such preset number is reached, for operating the flasher 518 and buzzer 520.

The counter reset circuit 68 provides facilities for starting and completing each counting cycle in clear areas which do not contain holes to avoid counting errors which could occur in the event the laminate 32 shifts or skews as it passes the light beam 50. This technique uses known information regarding the location of tool holes 40c and X-slots 42a in the laminate 32 and the number of tool holes within a given distance.

While the embodiment of the system 46 described herein is used to count holes and slots in the flexible laminate 32, it could be used to count holes in any substrate, flexible or rigid, in the same manner as described above. For example, when counting holes in rigid laminate, there is no need to control the punching operation since the rigid laminates are indexed through the punch press 44 or a drilling machine (not shown) and the system 46 on separate occasions. Moreover, there is no need for indications of circuit-section failure because the rigid laminates do not include successive circuit sections. Switch 420-1 (FIG. 11C) is closed to indicate if one failure occurs which activates the flasher 518 and buzzer 520 (FIG. 6). An additional counter, comparator, indicator and rotary switch may be needed in the counter-comparator circuit 88 (FIG. 11) to facilitate the counting up to 99,999 holes and slots.

Further, the principle of counting holes and detecting missing holes as used by the system 46 could be used to count and detect other properties. For example, if an article contained defects of a light-reflective property which is different from the light-reflective property of the remaining portion of the article, a light source could be directed onto the defect-containing surface of the article and the surface scanned by a light-sensor in the manner described above with respect to the system 46. The response of the system 46 would be the same as described above. Thus, the only difference would be in the properties of the article being scanned.

What is claimed is:

1. A method of automatically adjusting a threshold level of a pulse generating circuit in response to light emanating from a light-emittable area in a web, which comprises the steps of:
    passing successive scans of light from a light source over the light-emittable area of the web with repetitive scan cycles;
    sensing the amount of light emanating from the light-emittable area;
    developing a light pulse having a level proportional to the amount of light sensed;
    establishing a threshold level;
    comparing the level of the light pulse with the threshold level;
    producing a threshold pulse when the light pulse level exceeds the threshold level; and
    reducing the threshold level in response to the threshold pulse so that subsequent light pulses produce threshold pulses when the reduced threshold level is exceeded.

2. A method of automatically adjusting a threshold level of a pulse generating circuit in response to light emanating from a hole in a web, which comprises the steps of:
    passing successive scans of light from a light source over one side of the web with repetitive scan cycles whereby light is directed through the hole when the hole is coincident with the scans;
    sensing the amount of light directed through the hole;
    developing a light pulse having a level proportional to the amount of the light sensed;
    establishing a threshold level;
    comparing the level of the light pulse with the threshold level;
    producing a threshold pulse when the light pulse level exceeds the threshold level; and
    reducing the threshold level in response to the threshold pulse so that subsequent light pulses produce threshold pulses when the reduced threshold level is exceeded.

3. A method of automatically adjusting a threshold level of a pulse generating circuit in response to light emanating from a plurality of holes in a web and of counting each of the plurality of holes in the web, which comprises:
    passing successive scans of light from a light source over one side of the web with repetitive scan cycles whereby light is directed through holes coincident with the scans;
    sensing the amount of light directed through the hole;
    developing a light pulse having a voltage level proportional to the amount of light sensed;
    establishing a voltage threshold level;
    comparing the level of the light pulse with the threshold level;
    producing a threshold pulse when the light pulse level exceeds the threshold level;

reducing the threshold level in response to the threshold pulse so that subsequent light pulses produce threshold pulses when the reduced threshold level is exceeded;

storing each threshold pulse developed for each hole during the scan for a period equal to the time of a single scan cycle;

comparing each stored threshold pulse with the corresponding time frame of the next succeeding scan; and developing a single count pulse for each hole in the web when no pulse is developed in the corresponding time frame of the next succeeding scan during the time when the stored pulse is being compared with the corresponding time frame.

4. The method as set forth in claim 3 which further comprises the steps of:

accumulating the total count of count pulses developed in response to light-sensed holes;

comparing the accumulated total count with a predetermined count to ascertain whether the total number of holes in the web matches, or is a mismatch with, a predetermined count; and feeding the mismatch-developed pulse to an indicator to provide indication of the mismatch.

5. A system for automatically adjusting a threshold level of a pulse generating circuit in response to light emanating from a light-emittable area of a web, which comprises:

a light source;

means for passing successive scans of light from the source over the light-emittable area of the web with repetitive scan cycles;

means for sensing the amount of light emanating from the light-emittable area;

means for developing a light pulse having a level proportional to the amount of light sensed;

means for establishing a threshold level;

means for comparing the level of the light pulse resulting from the light-emittable area with the threshold level and for producing a threshold pulse when the light pulse level exceeds the threshold level; and means responsive to the threshold pulse for reducing the threshold level so that, in response to the next light pulse resulting from the light-emittable area, the comparing and producing means produces a threshold pulse when the reduced threshold level is exceeded.

6. A system for automatically adjusting a threshold level of a pulse generating circuit in response to light emanating from a hole in a web, which comprises:

a light source;

means for passing successive scans of light over one side of the web with repetitive scan cycles to direct light through the hole when the hole is coincident with the scans;

means for sensing the amount of light directed through the hole;

means for developing a light pulse having a level proportional to the amount of light sensed;

means for establishing a threshold level;

means for comparing the level of the light pulse resulting from the hole with the threshold level and for producing a threshold pulse when the light pulse level exceeds the threshold level; and means responsive to the threshold pulse for reducing the threshold level so that in response to the next light pulse resulting from the hole, the comparing and producing means produces a threshold pulse when the reduced threshold level is exceeded.

7. A system for automatically adjusting a threshold level of a pulse generating circuit in response to light emanating from a plurality of holes in a web and for counting each of the plurality of holes in the web, which comprises:

a light source;

means for passing successive scans of light over one side of the web with repetitive scan cycles to direct light through holes coincident with the scans;

means for sensing the amount of light directed through the holes;

means for developing a light pulse having a voltage level proportional to the amount of light sensed through each hole during each scan, the developed pulse of each hole being located within a time frame of the scan, the time frame being representative of the potential location of the hole along the scan;

means for establishing a voltage threshold level;

means for comparing the voltage level of the light pulse resulting from the hole with the threshold level and for producing a threshold pulse when the light pulse level exceeds the threshold level;

means responsive to the threshold pulse for reducing the threshold level so that, in response to the next light pulse resulting from the hole, the comparing and producing means produces a threshold pulse when the reduced threshold level is exceeded;

means for storing each threshold pulse developed for each hole during the scan for a period equal to the time of a single scan cycle; and means for comparing each stored threshold pulse with the corresponding time frame of the next succeeding scan and for developing a single count pulse for each hole in the web when no pulse is developed in the corresponding time frame of the next succeeding scan during the time when the stored pulse is being compared with the corresponding time frame.

8. The system as set forth in claim 7 which further comprises:

means for accumulating the total count of the count pulses developed in response to light-sensed holes;

means for comparing the accumulated total count with a predetermined count to ascertain whether the total number of holes in the web matches, or is a mismatch with, the predetermined count;

means for developing a pulse in response to a mismatch between the accumulated total count and predetermined count; and means for feeding the mismatch-developed pulse to an indicator to provide indication of the mismatch.

9. A system for automatically adjusting a threshold level of a pulse generating circuit in response to light emanating from a plurality of holes in a web and for counting each of the plurality of holes in the web, which comprises:

a light source;

means for passing successive scans of light over one side of the web with repetitive scan cycles to direct light through holes coincident with the scans;

means for sensing the amount of light directed through holes;

means for developing a train of light pulses in response to the sensing of light through a plurality of holes during a single scan, each of the developed light pulses being located within an associated one of successive time frames on the scan, each of the time frames being representative of the potential location of an associated one of the holes along the scan;

means for establishing a voltage threshold level;

means for comparing the voltage level of each of the train of light pulses with the threshold level and for producing a threshold pulse when the level of each of the train of light pulses exceeds the threshold level to thereby produce a corresponding train of threshold pulses;

means responsive to the train of threshold pulses for reducing the threshold level so that, when levels of light pulses of the next subsequent train exceed the reduced threshold level, another train of threshold pulses is produced;

means for storing each train of developed threshold pulses for a period equal to the time of a single time frame; and means for comparing the train of stored threshold pulses with the corresponding successive time frames of the next succeeding scan and for developing a single count pulse for each hole in the web when no pulse is developed in any of the corresponding time frames of the next succeeding scan during the time when the related one of the train of stored threshold pulses is being compared with the corresponding time frame.

10. A system for automatically adjusting a threshold level of a pulse generating circuit in response to light emanating from a hole in a web, which comprises:

a light source;

means for passing successive scans of light across one surface of the web with repetitive scan cycles to direct light through the hole when the hole is coincident with the scans;

a photocell for sensing the amount of light directed through the hole and for developing a light pulse having a voltage level proportional to the amount of light sensed;

an amplifier for increasing the voltage level of the light pulse;

a voltage threshold level establishing circuit;

a comparator having the amplifier coupled to one input thereof and the threshold level establishing circuit coupled to the other input thereof, the comparator generating a threshold pulse when the level of the light pulse exceeds the threshold level;

a delay circuit for delaying the threshold pulse for a period equal to the time of one scan cycle; and a threshold adjust circuit, responsive to the output of the delay circuit, for reducing the threshold level of the establishing circuit so that, in response to the next light pulse resulting from the hole, the comparator generates a threshold pulse when the reduced threshold level is exceeded.

11. A system as set forth in claim 10 wherein the threshold establishing circuit comprises a voltage divider network which is coupled to an input of the comparator to establish the threshold level.

12. A system as set forth in claim 11 wherein the threshold adjust circuit comprises a transistor which is coupled to the output of the delay circuit and the voltage divider network of the establishing circuit so that, when the transistor receives the threshold pulse from the delay circuit, the transistor conducts and reduces the level of voltage across the divider network thus reducing the threshold level within the comparator.

13. A system as set forth in claim 12 wherein the light source comprises a laser.

14. A system as set forth in claim 13 wherein the passing means comprises a rotating polyhedral mirror.

* * * * *